(12) United States Patent
Becker

(10) Patent No.: US 8,968,269 B2
(45) Date of Patent: Mar. 3, 2015

(54) MULTI-CONDUIT BALLOON CATHETER

(75) Inventor: Bruce B. Becker, Malibu, CA (US)

(73) Assignee: Acclarent, Inc., Menlo Park, CA (US)

(*) Notice: Subject to any disclaimer, the term of this patent is extended or adjusted under 35 U.S.C. 154(b) by 7 days.

(21) Appl. No.: 13/353,154

(22) Filed: Jan. 18, 2012

(65) Prior Publication Data

US 2012/0172835 A1 Jul. 5, 2012

Related U.S. Application Data

(60) Division of application No. 11/243,468, filed on Oct. 4, 2005, now Pat. No. 8,114,113, and a continuation-in-part of application No. 11/233,955, filed on Sep. 23, 2005, now abandoned.

(51) Int. Cl.
*A61M 31/00* (2006.01)
*A61M 3/02* (2006.01)
(Continued)

(52) U.S. Cl.
CPC .............. *A61M 25/10* (2013.01); *A61M 3/0283* (2013.01); *A61M 25/1002* (2013.01); *A61M 25/0041* (2013.01); *A61M 1/0084* (2013.01); *A61M 25/0032* (2013.01); *A61M 2210/0618* (2013.01); *A61M 2210/0681* (2013.01);
(Continued)

(58) Field of Classification Search
CPC ..................... A61M 25/0041; A61M 25/0043; A61M 25/0068; A61M 25/0069; A61M 25/0102; A61M 25/10; A61M 2025/0063; A61M 2039/0279; A61M 2210/0618
USPC ........................................... 604/48, 500, 514
See application file for complete search history.

(56) References Cited

U.S. PATENT DOCUMENTS

| 446,173 A | 2/1891 | Hancock |
| 504,424 A | 9/1893 | De Pezzer |
| 513,667 A | 1/1894 | Buckingham |
| 705,346 A | 7/1902 | Hamilton |

(Continued)

FOREIGN PATENT DOCUMENTS

| CH | 668188 | 12/1988 |
| CN | 2151720 | 1/1994 |

(Continued)

OTHER PUBLICATIONS

Argon Medical. Maxxim Medical. Ad for Sniper EliteTM Hydrophilic Ni—Ti Alloy Guidewire (2001).

(Continued)

*Primary Examiner* — Aarti B Berdichevsky
(74) *Attorney, Agent, or Firm* — Frost Brown Todd LLC

(57) ABSTRACT

A suctioning and irrigating sinus balloon catheter is provided for treating a patient's paranasal sinus system, including dilating prepared openings, and natural ostia and ducts and excising sinus cavities and choana. The catheter has a number of fluid carrying conduits to provide irrigation, suction and inflation/deflation to the distally mounted balloon. The catheters have sufficient stiffness and column strength that the balloon carrying distal segment of the catheter can be pushed into the prepared opening, natural ostium or duct, choana or sinus to be excised. Some catheters can be hand bendable by the surgeon. Some catheters provide the capability of threading an endoscope through one of the conduits. The methods use the balloon catheters to dilate prepared openings to selected parts of the sinus system, to dilate natural ostia and ducts of the sinus system, choana, and/or to dilate sinus cavities to remove them.

16 Claims, 12 Drawing Sheets

(51) Int. Cl.
*A61M 1/00* (2006.01)
*A61M 25/10* (2013.01)
*A61M 25/00* (2006.01)

(52) U.S. Cl.
CPC ............... *A61M 2025/0008* (2013.01); *A61M 2025/1061* (2013.01); *A61M 3/0295* (2013.01)
USPC ........................................................ 604/514

(56) References Cited

U.S. PATENT DOCUMENTS

| | | |
|---|---|---|
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robinson |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |

(56) References Cited

U.S. PATENT DOCUMENTS

| | | |
|---|---|---|
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wttermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-haim |
| 5,571,086 A | 11/1996 | Kaplan et al. |
| 5,578,007 A | 11/1996 | Imran |
| 5,578,048 A | 11/1996 | Pasqualucci et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |

(56) References Cited

U.S. PATENT DOCUMENTS

| | | |
|---|---|---|
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterwreck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |

(56) References Cited

U.S. PATENT DOCUMENTS

| | | |
|---|---|---|
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,923,827 B2 | 8/2005 | Campbell et al. |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |

(56) References Cited

U.S. PATENT DOCUMENTS

| | | |
|---|---|---|
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Rossner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,535,707 B2 | 9/2013 | Arensdorf et al. |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0016564 A1* | 2/2002 | Courtney et al. .......... 604/96.01 |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0064150 A1* | 4/2004 | Becker .......... 606/196 |
| 2004/0068242 A1* | 4/2004 | McGuckin, Jr. .......... 604/272 |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0159645 A1 | 7/2005 | Bertolero et al. |
| 2005/0182319 A1 | 8/2005 | Glossop |
| 2005/0234507 A1 | 10/2005 | Geske et al. |
| 2005/0240147 A1* | 10/2005 | Makower et al. .......... 604/96.01 |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0063973 A1 | 3/2006 | Makower et al. |
| 2006/0165926 A1 | 7/2006 | Weber |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |

(56) References Cited

U.S. PATENT DOCUMENTS

| | | |
|---|---|---|
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0171301 A1 | 7/2009 | Becker |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174308 A1 | 7/2010 | Chang et al. |
| 2010/0198191 A1 | 8/2010 | Clifford et al. |
| 2010/0198302 A1 | 8/2010 | Shalev |
| 2010/0274188 A1 | 10/2010 | Chang et al. |
| 2010/0290244 A1 | 11/2010 | Nath |
| 2011/0166190 A1 | 7/2011 | Anderson et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 96/29071 | 9/1996 |
| WO | WO 97/21461 | 6/1997 |
| WO | WO 99/24106 | 5/1999 |
| WO | WO 99/30655 | 6/1999 |
| WO | WO 99/32041 | 7/1999 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

(56) References Cited

OTHER PUBLICATIONS

Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. Www.inventors.about.com/library/inventors/blcatheter.htm?p=l.
Benninger et al.; Adult Chronic Rhinosinusitis: Defintions, Diagnosis, Epidemiology, and Pathophysilogy Arch Otolarygol Head and Neck Surg. vol. 129 (Sep. 2003) p. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W, et al. 'Nasal Systemic Drug Delivery', Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cachet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.

Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. '$\beta$-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE. (Mar. 2001).
Gottmann, et al. 'Successful treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375-378.
Ingals, E.F. 'New Operation and Instruments for Draining the Frontal Sinus' Ann. Otol, Rhinol. Layyngol. vol. 14 (1905) pp. 644-649.

(56) References Cited

OTHER PUBLICATIONS

Iro, H. et al., 'A New Device for Frontal Sinus Endoscopy: First Clinical Report' Otolaryngol. Head Neck Surg. (2001) vol. 125 No. 6 pp. 613-616.

Jacobs, J.B. '100 Years of Frontal Sinus Surgery' Laryngoscope. vol. 107 (1997) pp. 1-36.

K-Splints Internal Nasal Splints; Jan. 25, 2007; www.invotec.net/rhinology/ksplint.html.

Kaiser, H. et al 'Cortizontherapie, Corticoide in Klinik and Praxis' Thieme, Stuggart (1992) pp. 390-401.

Kennedy, D.W., M.D. et al. 'Diseases of the Sinuses: Diagnosis and Management' (Copyright 2001) by B.C. Decker Inc.

Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.

Kingdom, T.T. et al. 'Image-Guided Surgery of the Sinuses: Current Technology and Applications' Otolaryngol. Clin. North Am. vol. 37, No. 2 (Apr. 2004) pp. 381-400.

Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.

Kozlov et al. 'Diagnosis and Treatment of Sinusitis by YAMIK Sinus Catheters' Rhinology (1996) vol. 34, pp. 123-124.

Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.

Laliberte, F. et al. 'Clinical and Pathologic Methods to Assess the Long-Term Safety of Nasal Corticosteroids' Allergy. vol. 55, No. 8 (2000) pp. 718-722.

Lang, E.V., et al., 'Access Systems for Puncture at an Acute Angle' J. Vasc. Interv. Radiol. (1995) vol. 6, No. 5 pp. 711-713.

Lanza, D.C. 'Postoperative Care and Avoiding Frontal Recess Stenosis' International Advanced Sinus Symposium Jul. 21-24, 1993.

Large, G.C. 'Crystalline Tetracycline Hydrochloride in the Treatment of Acute and Chronic Maxillary Sinusitis' Canad. M.A.J. (1958) vol. 79 pp. 15-16.

Lund, V.J. 'Maximal Medical Therapy for Chronic Rhinosinusitis' Otolaryngol Clin N. Am. vol. 38 (2005) pp. 1301-1310.

Maran, A.G.D. et al. 'The Use of the Foley Balloon Catheter in the Tripod Fracture' J. Laryngol. Otol. (1971) vol. 85, Issue 9, pp. 897-902.

May, M. et al. 'Frontal Sinus Surgery: Endonasal Drainage Instead of an External Osteopolstic Approach' Op Tech Otolaryngo Head Neck Surgery. 6 (1995) pp. 184-192.

Medtronic, xomed.com-MicroFrance Catalog Browser. Www.xomcat.com/xomfrance/index.php?zone=both&cat=18&sub=58&prodline=1272 (Dec. 31, 2003) pp. 1-2.

Mehan, V.K. et al., 'Coronary Angioplasty through 4 French Diagnostic Catheters' Cathet. Cardiovasc. Diagn. (1993) vol. 30, No. 1 pp. 22-26.

Mellor, J.M. et al 'Synthesis of Trifluromethylnaphthalenes' Tetrahedron. vol. 56 (2000) pp. 10067-10074. Elsevier Science Ltd.

Metson, R., et al., 'Endoscopic Treatment of Sphenoid Sinusitis' Otolaryngol. Head Neck Surg. (1996) vol. 114, No. 6 pp. 736-744.

Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.

Miller, et al. 'Management of Fractures of the Supraorbital Rim' Journal of Trauma. vol. 18, No. 7 (Jul. 1978) pp. 507-512.

Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.

Mols, B. 'Movable Tool Tip for Keyhole Surgery' Delft Outlook, vol. 3 (2005) pp. 13-17.

Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.

Nasal Surgery and Accessories, Jan. 25, 2007; www.technologyforlife.com.au/ent/nasal.html.

Park, K. et al. 'Biodegradable Hydrogels for Drug Delivery' (1993) Technomic Publishing Inc. Lancaster.

Peirs, et al. 'A Flexible Distal Tip with Two Degrees of Freedon for Enhanced Dexterity in Endoscopic Robot Surgery' Proceedings 13th Micromechanics Europe Workshop (2002) pp. 271-274.

Piccirillo, J.F. et al. 'Physchometric and Clinimetric Validity of the 20-Item Sino-Nasal Outcome test (SNOT-20)' Copyright 1996 Washington University, St. Louis, MO.

Podoshin, L et al. 'Balloon Technique for Treatment of Frontal Sinus Fractures' The journal of Laryngology & Otology (1967), vol. 81. pp. 1157-1161.

Pownell, P.H. et al., 'Diagnostic Nasal Endoscopy' plastic & Reconstructive Surgery (1997) vol. 99, Iss5 pp. 1451-1458.

Prince, et al. 'Analysis of the Intranasal Distribution of Ointment' J Otolaryngol. vol. 26 (1997) pp. 357-360.

Ramsdale, D.R., Illustrated Coronary Intervention: A case-oriented approach, (2001) Martin Dunitz Ltd. pp. 1-5.

Ritter, F.N. et al., Atlas of Paranasal Sinus Surgery (1991) Igaku-Shoin Medical Pub. pp. 1-81.

Robison, J. Mathews, M.D. 'Pressure Treatment of Maxillary Sinusitis' J.A.M.A. (May 31, 1952) pp. 436-440.

Robison, J. Mathews, M.D. 'Pressure Treatment of Purulent Maxillary Sinusitis' Texas State Journal of Medicine (May 1952) pp. 281-288.

Sama, A., et al., 'Current Opinions on the Surgical Management of Frontal Sinus Disease' ENT News. Www.pinpointmedical.com/ent-news (2009) vol. 17, No. 6 pp. 60-63.

Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.

Sawbones Catalog 2001, Pacific Research Laboratories, Inc., Vashon Washington 98070 USA.

Saxon, R.R. et al., 'Technical Aspects of Accessing the Portal Vein During the TIPS Procedure' J. Vasc. Interv. Radiol. (1997) vol. 8, No. 5 pp. 733-744.

Schaefer, S.D., M.D. 'Rhinology and Sinus Disease: A Problem-Oriented Approach' (Copyright 1988) by Mosby, Inc.

Schneider. Pfizer Ad for Softip [date of publication unknown].

Shah, N.J. et al., 'Endoscopic Pituitary Surgery—A Beginner's Guide' Indian Journal of Otolaryngology and Head and Neck Surgery (2004) vol. 56, No. 1 pp. 71-78.

Shah, N.J. 'Functional Endoscopic Sinus Surgery' (1999); found at bhj.org/journal/1999_4104_oct99/sp_659.htm.

Single -Pole and Multi-Pole Lightguides for UV Spot Light Curing Systems. Www.dymax.com/products/curing_equipment/lightguids/light. (2004) pp. 1-2.

Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.

St. Croix, et al., 'Genes Expressed in Human Tumor Endothelium' Science (May 15, 2000) vol. 289 pp. 1197-1202.

Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.

Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.

Strohm, et al. Die Behandlung von Stenosen der oberen Luftwege mittels rontgenologisch gesteuerter Ballondilation (Sep. 25, 1999) pp. 1-4.

Strohm, et al. 'Treatment of Stenoses of the Upper Airways by Balloon Dilation' Sudwestdeutscher Abstract 45 (Sep. 25, 1999) pp. 1-3.

(56) References Cited

OTHER PUBLICATIONS

SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiner's First Report, dated Apr. 8, 2010 for AU 2005274794.
European Communication dated Sep. 4, 2008 for Application No. EP 05773189.
European Communication dated Jun. 19, 2009 for Application No. EP 05773189.
European Exam Report dated Feb. 22, 2006 for Application No. 02716734.5.
European Exam Report dated Feb. 8, 2007 for Application No. 02716734.5
Supplemental European Search Report and Written Opinion dated Sep. 11, 2009 for Application No. EP 06815174.
European Search Report dated Mar. 16, 2010 for Application No. EP 06718986.
European Search Report dated Sep. 27, 2011 for Application No. EP 10182961.
European Search Report dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental European Search Report dated Jun. 2, 2008 for Application No. EP 05773189.
Supplemental Partial European Search Report dated Jul. 1, 2009 for Application No. EP 06815285.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental Partial European Search Report dated Nov. 19, 2010 for Application No. EP 06751637.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report dated Dec. 6, 2007 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/36960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report and Written Opinion dated Aug. 17, 2007 for Application No. PCT/US05/13617.
International Search Report dated Aug. 29, 2007 for Application No. PCT/US06/002004.
International Search Report dated Sep. 25, 2007 for Application No. PCT/US06/37167.
International Search Report dated Oct. 19, 2007 for Application No. PCT/US07/03394.
International Search Report and Written Opinion dated May 29, 2008 for Application No. PCT/US07/021170.
International Search Report dated May 29, 2008 for Application No. PCT/US07/21922.
International Search Report and Written Opinion dated Jul. 1, 2008 for Application No. PCT/US06/22745.
International Search Report dated Jul. 3, 2008 for Application No. PCT/US2006/029695.
International Search Report dated Jul. 7, 2008 for Application No. PCT/US07/16213.
International Search Report dated Jul. 8, 2008 for Application No. PCT/US07/11474.
International Search Report dated Jul. 17, 2008 for Application No. PCT/US06/36960.
International Search Report and Written Opinion dated Jul. 21, 2008 for Application No. PCT/US05/33090.

(56) References Cited

OTHER PUBLICATIONS

International Search Report dated Aug. 25, 2008 for Application No. PCT/US2008/000911.
International Search Report dated Sep. 10, 2008 for Application No. PCT/US07/16212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/11449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
English Machine Translation of Japanese Patent Publication No. JP 5-211985.
English Machine Translation of Japanese Patent Publication No. JP 6-277296.
English Machine Translation of Japanese Patent Publication No. JP 8-317989.
English Machine Translation of Japanese Patent Publication No. JP 10-024098.
English Machine Translation of Japanese Patent Publication No. JP 11-507251.
English Machine Translation of Japanese Patent Publication No. JP 2000-501634.
English Machine Translation of Japanese Patent Publication No. JP-2001-501846.
English Machine Translation of Japanese Patent Publication No. JP 2002-508214.
English Machine Translation of Japanese Patent Publication No. JP 2002-537908.
English Machine Translation of Japanese Patent Publication No. JP 2002-538850.
English Machine Translation of Japanese Patent Publication No. JP 2003-062080.
English Machine Translation of Japanese Patent Publication No. JP 2004-357728.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO File History of Patent No. 7,462,175.
U.S. Appl. No. 11/233,955, filed Sep. 23, 2005.
U.S. Appl. No. 11/789,705, filed Apr. 24, 2007.
U.S. Appl. No. 60/844,874, filed Sep. 15, 2006.
U.S. Appl. No. 60/922,730, filed Apr. 9, 2007.

(56) References Cited

OTHER PUBLICATIONS

U.S. Appl. No. 61/052,413, filed May 12, 2008.
U.S. Appl. No. 61/084,949, filed Jul. 30, 2008.
U.S. Appl. No. 61/165,448, filed Mar. 31, 2009.
European Communication dated Nov. 29, 2010 for Application No. EP 06 815 285.9.
European Communication dated Nov. 11, 2011 for Application No. EP 06 815 285.9.

* cited by examiner

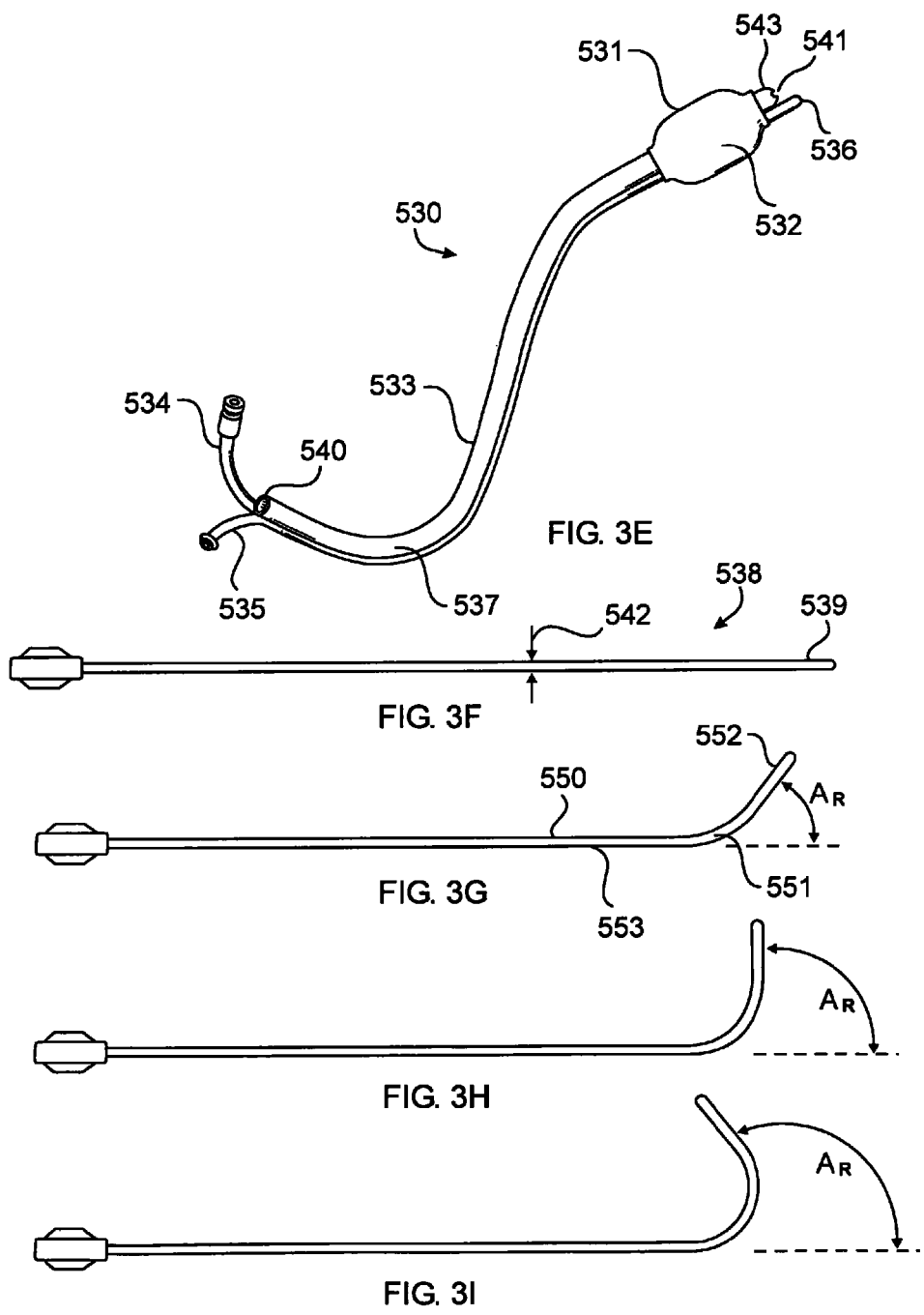

MULTI-CONDUIT BALLOON CATHETER

PRIOR APPLICATION

The present application is a divisional of U.S. patent application Ser. No. 11/243,468, filed Oct. 4, 2005, issued as U.S. Pat. No. 8,114,113, which is a continuation-in-part of U.S, patent application Ser. No. 11/233,955 filed Sep. 23, 2005, now abandoned.

FIELD OF THE INVENTION

This invention relates to balloon catheters and methods using such catheters for treating paranasal sinuses.

BACKGROUND

To fully understand the invention, it is necessary to consider the anatomy and physiology of the nasal and sinus system. FIGS. 4-17, which show various method steps described later, also show important features of sinus anatomy. The maxillary sinus 21 lies lateral to the nasal cavity 38, inferior to the eye orbit 23 and superior to the palate or roof of the mouth. The medial wall of the maxillary sinus forms the lateral nasal wall 44 inferiorly. The frontal sinus 35 (FIG. 16) lies above the orbit and its floor is formed by the frontal bone and is contiguous with part of the orbital roof. The right and left frontal sinuses are divided by the interfrontal septum. The frontal sinus drains into the nasal cavity and its outflow tract is in the inferomedial sinus, which connects to the frontonasal duct 36. Frontonasal duct 36 empties into the nasal cavity through lateral nasal wall 44 under the middle turbinate 20.

The ethmoid sinus is divided into anterior and posterior ethmoid air cells 29 and 31. The ethmoid sinus consists of multiple spaces or cells divided by thin bony septae. The ethmoid sinus is contained in the ethmoid bone. The lateral wall of the ethmoid sinus composes the medial wall of the orbit. The medial wall of the ethmoid sinus composes the lateral wall 44 of the nasal cavity superiorly. Anterior ethmoid air cells 29 drain through lateral nasal wall 44 into the middle meatus 22 beneath middle turbinate 20.

The sphenoid sinus 39 (FIG. 15) is posterior to the ethmoid sinus 29 and 31. Sphenoid sinus 39 has a lateral wall that is adjacent to the optic nerve, carotid artery, and cavernous sinus. The floor of sphenoid sinus 39 lies above maxillary sinus 21 and pterygopalatine fossa. Lateral nasal wall 44 is partially covered by inferior 46, middle 20, and superior 17 turbinates.

The choanae (FIG. 17) are the posterior openings of the nose. Each choana 299 is separated by the vomer bone. The lateral border of the choana is formed by the posterior end of the turbinates.

Sinus physiology will now be considered. The mucosa of nasal cavity 38 contains secretory elements (mucosal glands and goblet cells) and a dense ciliary layer. The paranasal sinuses are covered by a similar mucosa, although the secretory cells and cilia may be sparser in the more remote areas of the sinuses. The secretory cells produce a large volume of mucus that is normally actively transported by the cilia (mucociliary transport) in a specific pattern (not a gravity dependant pattern) from the sinus through the opening between the sinus and the nasal cavity (sinus ostium). Cellular debris and bacteria are transported in the mucus from the sinus cavity through the ostium into the nose.

Inflammation of the sinus and nasal mucosa causes hyperemia, lymphatic swelling, stasis in the blood and lymphatic pathways and leads to increased secretion of mucus and reduced mucociliary transport. The inflammation may be caused by allergies, noxious agents, nasal polyps, and other factors. Over time, there is a pathologic increase in inflammatory cells, ground substance, and fibers with a permanent disruption of mucociliary transport and lymphatic drainage. An obstruction of the narrow ducts and ostia between the paranasal sinuses and nasal cavity develops, resulting in a vicious cycle of increased secretions, edema, and ultimately organized connective tissue and mucosal hyperplasia. Bacteria are not cleared from the sinuses and multiply in the fertile inflammatory environment worsening the chronic sinus inflammation (sinusitis).

Treatment with antibiotics, corticosteroids in nasal sprays or systemically, and antihistamines may result in resolution of sinusitis. However some patients become resistant to medical treatment and surgery becomes necessary.

Modern sinus surgery is usually performed endoscopically and is based on the principle of restoring patency of the sinus ducts and ostia by enlarging the opening and allowing mucociliay clearance of mucus from the sinus into the nose to resume. If mucociliary clearance is re-established, then the inflammatory changes in the sinus mucosa described above will resolve. In classic sinus surgery, an incision was made along the side of the nose in the medial canthus to access the ethmoid or sphenoid sinuses. This incision could be extended to beneath the medial half of the brow to also access the frontal sinus. An incision through the gums above the upper teeth and creation of a large bony opening in the maxilla with excision of large areas of sinus mucosa was used to perform maxillary sinus surgery. A large opening was created through the medial wall of the maxillary sinus into the nose in the inferior meatus (maxillary antrostomy) to allow postoperative drainage of the sinus.

The development of endoscopic sinus surgery allowed sinus surgery to be performed from an intranasal approach, thus eliminating the need for external incisions, the creation of very large bony openings, and reducing morbidity. However, endoscopic sinus surgery requires the excision of large areas of bone and nasal mucosa and has reported complications of blindness from damage to the optic nerve, double vision from damage to the orbit and medial rectus muscle, damage to the nasolacrimal duct resulting in tearing and dacryocstitis, leakage of cerebrospinal fluid and infection of the brain and meninges, loss of the sense of taste, infection of the skull base, hemorrhage from the carotid artery or other blood vessels, and pain and neuralgia of the face and scalp.

As shown in U.S. Pat. Nos. 5,021,043 and 5,169,043, I have previously co-invented balloon catheters for use in the lacrimal system. As shown in my U.S. patent application Ser. No. 10/259,630 and published under U.S. Pat. Pub. No. 20040064083 (now U.S. Pat. No. 7,169,163), I teach that a balloon catheter can be introduced transnasally to treat the lacrimal system.

As shown in my U.S. patent application Ser. No. 10/259, 300 and published under U.S. Pat. Pub. No. 20040064150 (now U.S. Pat. No. 8,317,816), incorporated herein by this reference, I teach that various balloon catheters can be used to treat paranasal sinuses in a number of ways. The catheters are used to dilate an existing ostium or duct, to create a new opening from a sinus to the nose, or to excise a sinus. However, blood, mucus or other material may obscure visualization when using a sinus balloon catheter. Also, other procedures such as excision of nasal or sinus tissue, polyps, mucoceles, or removal of pus, manipulation of the nasal or sinus structures would not be attempted using a balloon catheter because visualization and/or delivery of medication would be problematic.

Endoscopes have long been commercially available to provide the surgeon greater visualization of internal patient tissues. Endoscopes typically have a narrow, elongated body carrying fiber optic structures which allow viewing from a proximal eyepiece to a distal viewing lens and carry an illuminating ;light from a proximal source to a distal emitter. Endoscopes can have bodies which are rigid such as the KARL STORZ SINUSCOPE brand endoscope, or flexible such as the MACHIDA ENT SCOPE brand endoscope commercially available from Karl Storz, of Culver City, Calif. and Jedmed Instrument Company, of St. Louis, Mo. respectively. Endoscopes are typically not intended to bend sharper than a minimum radius. Some endoscopes can attach to a camera which can be joined to the endoscope at its proximal end. Some endoscopes have a viewing lens at the distal end which aims at an angle from the major axis of the endoscope body. This angle can range from 0 to 70 degrees. Many commonly used rigid endoscopes have an angle of about 25 or 30 degrees.

It has been found that the use of endoscopes simultaneously with irrigation and suction systems can be overly bulky in the small confines of some anatomical regions such as the nasal cavity or sinus. Further, using so many systems at once can leave the surgeon short handed.

Hand bending the balloon catheter body, though conveniently providing the surgeon with greater flexibility during surgery to adapt the catheter shape to the unique anatomy of the individual patient, can lead to additional problems. First, the catheter should remain sufficiently stiff to withstand the lateral or torsional forces required to push the deflated balloon section through the small opening in the tissue. Second, the surgeon may accidentally bend the catheter body beyond a maximum allowable angle, or at such a sharp radius that a flow constricting kink is created.

A review of the prior art shows a number of patents (Katz U.S. Pat. No. 6,027,478; Brennan U.S. Pat. No. 4,883,465; Akiyama U.S. Pat. No. 4,102,342; Payton U.S. Pat. No. 4,338,941; Katz U.S. Pat. No. 5,454,817; Stangerup U.S. Pat. No. 5,546,964 and Shippert U.S. Pat. No. 5,827,224) which teach the use of expandable devices (usually a balloon) into the nasal cavity or sinuses. Most of these are for the treatment of nose bleeds or the control of bleeding.

A number of articles disclose the use of a balloon catheter in sinuses to hold fractured bones in place, stop bleeding by tamponade, prevent fluid from flowing out of the nose into the pharynx, or to maintain a low intranasal air pressure. In one case, a catheter was used to stent a duct after surgery; and the balloon was inflated in the sinus to keep the stent in position.

However, apart from my prior application, there appear to be no teachings in the prior art to use a balloon catheter to create a new opening from a sinus into the nose, to dilate an ostium or duct, dilate the choana or excise a sinus. It appears a balloon has never been used to directly treat sinus disease.

SUMMARY

The present embodiments teach the use of sinus balloon catheters to treat sinus disease by creating a new opening from a sinus into the nose, to dilate a sinus ostium or duct, to dilate the choana or to excise a sinus. A balloon is mounted over the distal segment of the catheter to which runs a conduit permitting a pressurized fluid to inflate the balloon. The catheter is formed to have sufficient stiffness and column strength to be pushed through a surgically prepared small, tight opening from a sinus into the nose, through a sinus ostium or duct, or the choana or into a sinus cavity. The small opening may be created surgically or may be the natural ostium or duct of the sinus.

Some embodiments provide a catheter having integrated suction and/or irrigation systems that enable the surgeon to irrigate and/or suction away blood, mucus, pus, a mucocele and other material. The proximal end of the catheter has connectors to the various fluid supplies, suction sources, and wings or other prominences to allow the surgeon easier manipulation. The presence of suction and/or irrigation allows for the less obstructed use of an endoscope which greatly facilitates the surgeon visualizing the balloon catheter and the patient tissues in performance of the procedure.

Some embodiments provide a catheter having a conduit through which an endoscope can be inserted further reducing the bulkiness of the systems. Other embodiments provide an integrated endoscope in addition to the integrated suction and/or irrigation systems.

Balloon catheters having integrated suction, irrigation and endoscopic capability can be utilized to more efficiently and safely perform a number of procedures in the nasal cavity and sinus.

Other embodiments provide a set of catheters having different configurations and dimensions suitable for the treatment of different parts of the paranasal sinus system.

In other embodiments the balloon catheter has a proximal segment and a circular bend placing a distal segment at an angle of about 60 degrees to 130 degrees. The angled distal segment allows the surgeon to rotate or shift the position of the long proximal catheter shaft, thus positioning the distal segment to enter from the nasal cavity into the sinus at various angles appropriate to each individual patient. A catheter having an angle of approximately 90 degrees can be used to treat maxillary and frontal sinus disease.

Another embodiment provides a balloon catheter which is straight or has a minimal angle of about 0 to 60 degrees at the junction of the distal segment and the proximal segment. This catheter is useful for ethmoidectomy and sphenoid sinusotomy which uses a balloon with an inflated diameter of about 7 mm, or dilation of the choana and uses a balloon with an inflated diameter of about 9 mm.

Other embodiments provide balloon catheters having a sufficiently small deflated profile to fit through the sinus ostium, duct, or opening in the nasal wall or scar tissue into the sinus.

Other embodiments provide methods to open or enlarge an obstructed or narrowed ostium or duct of a sinus using a balloon and allow the sinus to drain into the nose. The methods also allow dilation and suction of a stenotic or atretic choana. The methods enable irrigation and suction as part of the sinus balloon catheters, and allow the use of an endoscope with the balloon catheter. The irrigation, suction, and endoscope provide better visualization by the surgeon in spite of bleeding or the presence of mucus or other debris. Such debris including pus or a mucocele can be suctioned from the sinus. Medication can also be introduced through the irrigation port. These procedures are accomplished without causing damage to the surrounding structures such as the optic nerve, extraocular muscles that move the eye, the orbit, brain, meninges, or nasolacrimal duct.

Other embodiments provide a method which removes a sinus and cures sinus disease without damage to the surrounding structures such as the optic nerve, extraocular muscles, orbit, brain, meninges, and nasolacrimal duct. These methods are useful for opening a sinus ostium or duct which has been narrowed or obstructed by scar tissue from previous surgery or trauma, for creating a new opening in the wall of a sinus which has scar tissue to allow proper drainage of the sinus into the nose, and for removing a sinus which has scar tissue.

Other embodiments provide methods including a balloon catheter antrostomy of the maxillary ostium, a balloon catheter middle meatal maxillary antrostomy, a balloon catheter inferior meatal antrostomy, a balloon catheter ethmoidectomy of the anterior ethmoid sinus, a balloon catheter ethmoidectomy of the posterior ethmoid sinus, a balloon catheter sinusotomy of the sphenoid sinus, a balloon catheter frontal sinusotomy, and balloon catheter dilation of the choana. These methods are improved by the greater visualization provided by an endoscope unobstructed by irrigatably suctionable debris.

In some embodiment there is provided a catheter for dilating a space in a patient, said catheter comprises: an oblong body having a proximal segment and a distal segment; a balloon member secured to said distal segment; a first conduit in fluid communication with said balloon, whereby fluid under a given pressure in said first conduit inflates said balloon; and, a second conduit having a distal port outside said balloon.

In some embodiments, said conduit is adapted to provide suction at said port. In some embodiments, said conduit is adapted to provide irrigation at said port. In some embodiments, said first and second conduits are formed into a multi-channel fluid buss extending between said proximal and distal segments. In some embodiments said first conduit terminates at a first conduit opening inside said balloon. In some embodiments said balloon has a substantially barbell shape when inflated. In some embodiments said second conduit has a distal terminus at said port and wherein said port is located a first distance from a distal neck of said balloon. In some embodiments said balloon annularly surrounds a portion of said second conduit. In some embodiments the catheter further comprises a third conduit having a distal port outside said balloon. In some embodiments said second conduit and said third conduit are coaxial. In some embodiments said second conduit and said third conduit are non-coaxial. In some embodiments the catheter has a stiffness which renders it hand bendable. In some embodiments the catheter has a stiffness which renders it non-hand bendable. In some embodiments said catheter has a bend. In some embodiments said balloon has a proximal neck extending over said bend. In some embodiments said body further comprises axial gradation markings. In some embodiments said second conduit has an inner diameter selected to allow passage of an endoscope therethrough. In some embodiments the catheter further comprises means for angularly securing said endoscope to said catheter. In some embodiments said means comprise at least one projection extending radially from a section of said endoscope. In some embodiments said catheter further comprises an angular orientation indicator. In some embodiments said second conduit is shaped to have an angular cutaway forming said port. In some embodiments said second conduit is formed of a stainless steel hypotube with a wall thickness of at least 0.010". In some embodiments said distal segment is at an angle of between about 0 degrees and about 130 degrees to said proximal segment. In some embodiments said distal segment is at an angle of between about 0 degrees and about 90 degrees to said proximal segment. In some embodiments said distal segment is at an angle of about 0 degrees to said proximal segment, whereby said catheter body is straight.

In some embodiments, there is provided a kit for use in the treatment of a patient's nasal sinuses, said kit comprises: a first balloon catheter having an oblong body; and, a catheter bending tool having a given bend radius and a first surface shaped and dimensioned to intimately contact and bear against a portion of said body. In some embodiments said given bend radius is at least 0.5 centimeter. In some embodiments said kit further comprises an endoscope having a minimum bend radius which is greater than said given bend radius of said tool.

In some embodiments, it is provided that in a sinus balloon catheter device comprising proximal and distal sections, a balloon mounted to said distal section, and a first conduit for inflating said balloon, an improvement which comprises a second conduit having a distal port outside said balloon.

In some embodiments, there is provided a balloon catheter for dilating a space in a patient's nasal sinus system, which is one of a prepared opening, an ostium or duct, or a sinus cavity to be excised, or choana, comprising: a tubular catheter body having a proximal end, a proximal segment, a distal end, and a distal segment; a balloon member disposed about said distal segment, said distal segment having a slot; said catheter body being closed at a point distally of said slot; means for applying fluid under pressure to said proximal end of said catheter body, said fluid under pressure flowing through said slot to inflate said balloon for dilating said space; and said catheter body being formed of a hypotube of sufficient stiffness and column strength to enable said catheter, when said inflatable member is deflated, to be pushed into said space of said nasal sinus system.

In yet other embodiments there is provided a method of treating a patient's nasal sinuses, comprising: providing a balloon catheter having an oblong body having a proximal segment, a distal segment, and a first inflation/deflation supply conduit in fluid communication with a balloon mounted on said distal segment; pushing said distal segment with said balloon deflated into a space associated with a nasal sinus of said patient; and introducing fluid under pressure into said supply conduit to inflate said balloon and dilate said space.

In some embodiments said balloon catheter further comprises a second conduit. In some embodiments the method further comprises suctioning debris from said nasal sinus through said second conduit. In some embodiments the method further comprises irrigating said nasal sinus through said second conduit. In some embodiments the method further comprises irrigating said nasal sinus through said second conduit at a time when said suctioning is not occurring. In some embodiments the method further comprises bending said body to an angle of between about 0 degrees and 130 degrees prior to said pushing. In some embodiments the method further comprises inserting an endoscope through said second conduit. In some embodiments said balloon catheter further comprises a third conduit, and wherein said method further comprises: suctioning debris from said nasal sinus through said second conduit; and, irrigating said nasal sinus through said third conduit. In some embodiments said body is flexible, and said method further comprises threading said body onto a rigidizing member having sufficient stiffness and column strength to enable said catheter, when said balloon is deflated, to be pushed into said space of said nasal sinus system. In some embodiments said tubular catheter body has a bend placing said distal segment at an angle of between about 60 degrees and about 130 degrees to said proximal segment. In some embodiments said angle is about 90 degrees.

In some embodiments of the method said space is the maxillary ostium of the patient's maxillary sinus, said distal segment with said balloon deflated being pushed through said maxillary ostium into said maxillary sinus, said maxillary ostium being dilated when said inflatable member is inflated to complete antrostomy of said maxillary ostium. In some embodiments, prior to said step of pushing said distal segment through said maxillary ostium, said method further comprises: medially retracting the patient's middle turbinate to gain access to the patient's middle meatus; and, exposing the patient's ethmoid infundibulum by removing part of the patient's uncinate process.

In some embodiments, said space is a prepared opening formed through the patient's fontanelle, said opening is formed by bringing a 45 degree upbiting Blakesely punch into the patient's nasal cavity along the patient's lateral nasal wall just superior to the patient's inferior turbinate, pushing said punch through said fontanelle to create said opening through said fontanelle and wherein said distal segment with said balloon deflated is pushed into said prepared opening and said balloon is inflated to dilate said prepared opening.

In some embodiments, said space is a prepared opening formed through the patient's lateral nasal wall in the patient's inferior meatus. In some embodiments, prior to said step of pushing, said prepared opening is formed by displacing the patient's inferior turbinate medially, introducing a sharp dissector into the patient's nasal cavity, and using said dissector to perforate the patient's lateral nasal wall in said inferior meatus to form said opening and wherein said distal segment with said balloon deflated is pushed into said prepared opening and said balloon is inflated to dilate said prepared opening. In some embodiments, said distal segment is positioned at an angle of between about 0 degrees and about 60 degrees to said proximal segment. In some embodiments, said distal segment is at an angle of about 0 degrees to said proximal segment, whereby said catheter body is substantially straight.

In some embodiments, said space is formed in the patient's ethmoid bulla. In some embodiments, the method further comprises: medially retracting the patient's middle turbinate to gain access to the patient's middle meatus; exposing the patient's ethmoid infundibulum by removing part of the patient's uncinate process; and, using a fine cutting forceps to remove the anterior wall of said ethmoid bulla. In some embodiments, after said inflatable member is deflated and withdrawn from said ethmoid bulla, providing said opening in said ethmoid bulla to receive said distal segment, which when inflated, dilates and thereby removes said ethmoid bulla. In some embodiments, said inflated balloon is then deflated and said distal segment is then withdrawn from the space formerly occupied by said ethmoid bulla, said distal segment with said balloon deflated is then pushed into the patient's anterior ethmoid air cells, forming the patient's ethmoid sinus, lying posterior to said space formerly occupied by said ethmoid bulla, said balloon is then inflated dilating said anterior ethmoid air cells and thereby removing said anterior ethmoid air cells, and said balloon is then deflated, and said distal segment is then removed from the space formerly occupied by said anterior ethmoid air cells, completing an ethmoidectomy of the anterior ethmoid sinus. In some embodiments, the patient's basal lamella of the patient's middle turbinate is perforated with a punch to form an opening, said distal segment is then pushed through said opening into said posterior ethmoid air cells and said balloon is inflated to dilate and remove said posterior ethmoid cells completing an ethmoidectomy of said posterior ethmoid sinus. In some embodiments, after said anterior and posterior ethmoidectomies are completed, inserting said distal segment through the patient's anterior wall of the patient's sphenoid sinus, the balloon is then inflated for dilation and opening of said sphenoid sinus, the deflating said balloon and removing said distal segment to complete sinusotomy of said sphenoid sinus.

In some embodiments, said space is an opening through the patient's anterior wall of the patient's sphenoid sinus; and wherein said method further comprises deflating said balloon and removing said distal segment to complete sinusotomy of said sphenoid sinus.

In some embodiments, said space is the patient's nasofrontal duct to the patient's frontal sinus; and wherein said method further comprises deflating said balloon and removing said distal segment to complete sinusotomy of said frontal sinus.

In some embodiments, after said ethmoidectomy of said anterior ethmoid sinus is completed and the patient's nasofrontal duct is exposed, providing a second balloon catheter having a tubular catheter body with a proximal segment, a distal segment, a balloon member mounted around said distal segment, a slot through the wall of said distal segment, said tubular body being closed at a point distally of said slot, and means providing fluid under pressure at the proximal end of said tubular catheter body to inflate said balloon, said tubular catheter body having a bend placing said distal segment at an angle of between about 60 degrees and about 130 degrees to said proximal segment, pushing said distal segment of said second balloon catheter with said balloon of said second balloon catheter deflated into said frontonasal duct, inflating second balloon catheter to dilate said frontonasal duct and frontal sinus, deflating said balloon of said second balloon catheter, and removing said distal segment of said second balloon catheter to complete a frontal sinusotomy.

In some embodiments, said space is a choana, said distal segment with said balloon deflated being pushed into the choana, said choana being dilated when said inflatable member is inflated.

In some embodiments, there is provided an apparatus for treating prepared openings and natural ostia or ducts providing flow paths from natural sinus cavities, and excising sinus cavities, comprising: a set of balloon catheters including catheters which are angled and catheters which are substantially straight, said catheters having appropriate inflated working diameters, and which have appropriate outer diameters with the balloon deflated that will enable the catheter in question to be pushed into the respective prepared opening, natural ostium or duct or sinus cavity to be excised.

BRIEF DESCRIPTION OF THE DRAWING

FIG. 3E is a diagrammatic perspective view of a flexible body multi-conduit balloon catheter according to another alternate embodiment.

FIG. 3F-FIG. 3I are diagrammatic side elevational view of of differently angled rigidizing members for providing rigidity to the catheter of FIG. 3E.

DESCRIPTION OF THE PREFERRED EMBODIMENTS

Figure 1A:
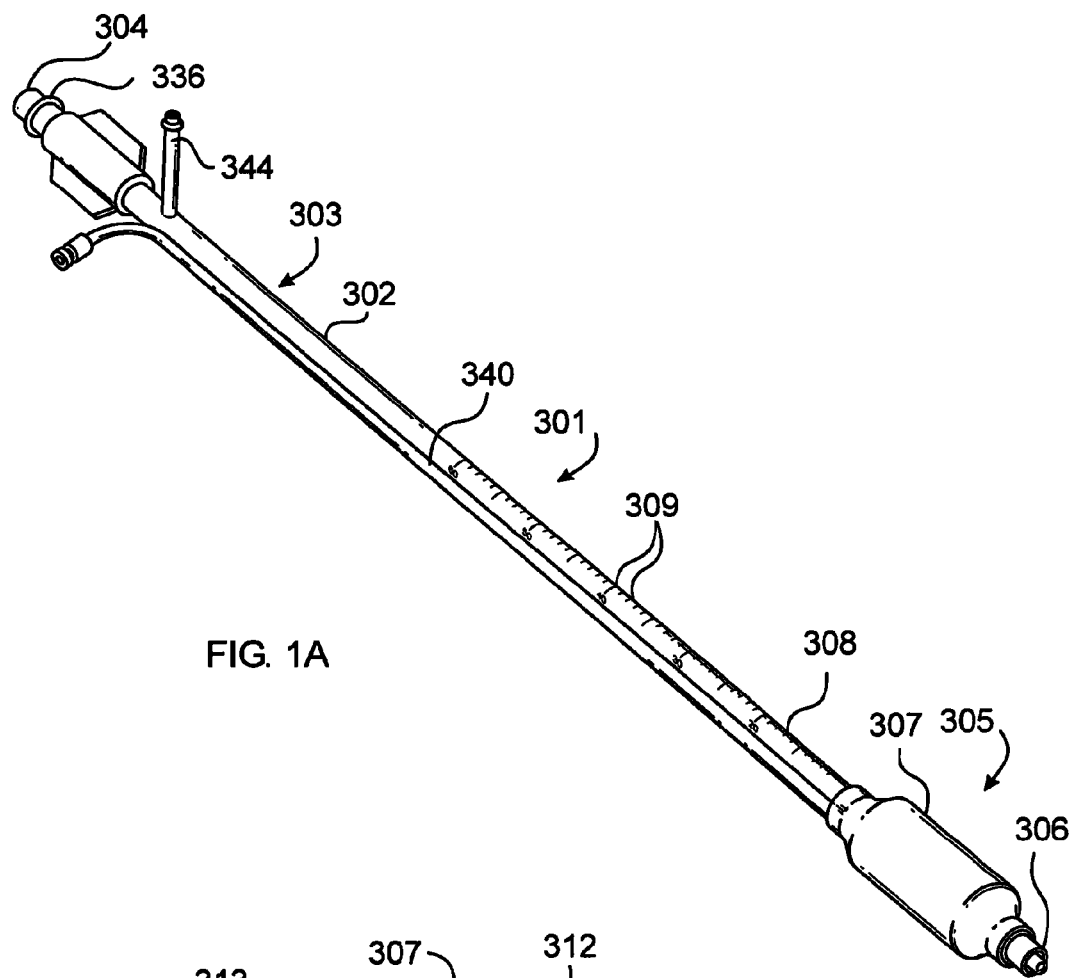
FIG. 1A is a diagrammatic perspective view of a suctioning and irrigating balloon catheter.
Figure 1B:
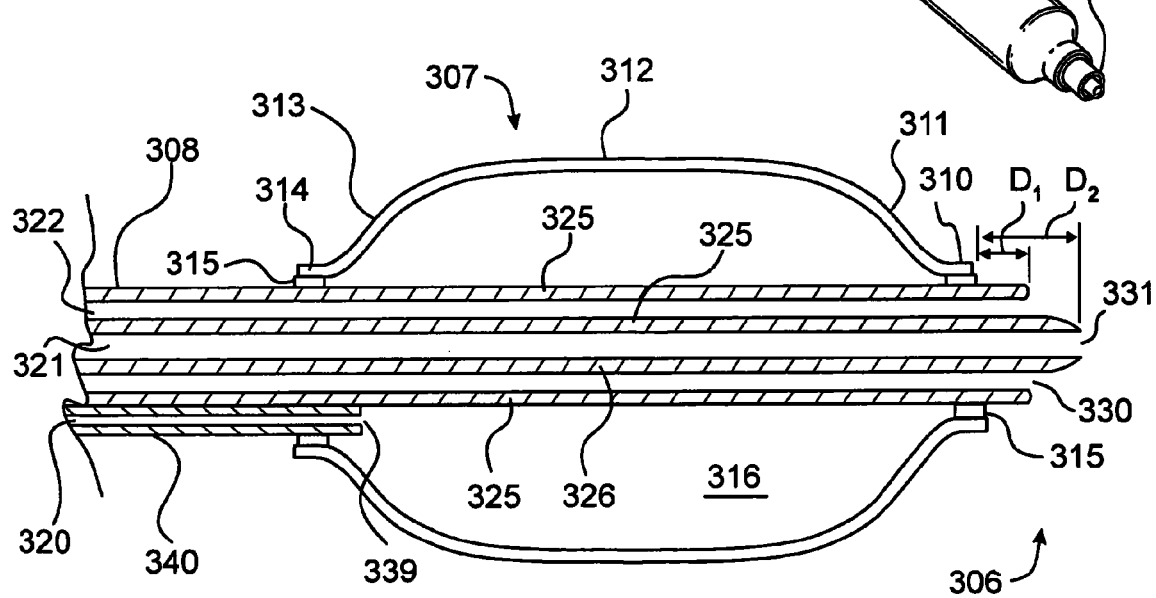
FIG. 1B is a closeup diagrammatic cross-section view of the tip of the distal segment of the suctioning and irrigating balloon catheter of FIG. 1A.
Figure 1C:
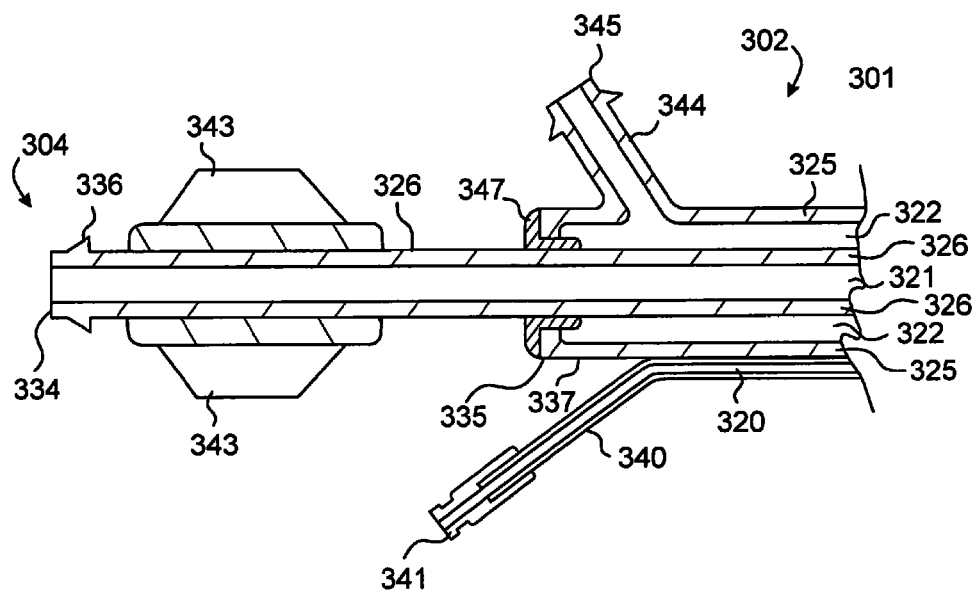
FIG. 1C is a closeup diagrammatic cross-section view of the proximal end segment of the suctioning and irrigating balloon catheter of FIG. 1A.

Referring now to the drawing there is shown in FIGS. 1A-1C, a first embodiment of a suctioning and irrigating sinus balloon catheter 301 having a generally oblong body 302 having a proximal segment 303, a proximal end 304, a distal segment 305 and a distal end 306. An inflatable balloon 307 is located on the distal segment of the body near the distal end.

The catheter body 302 has a given axial length as measured from proximal end to distal end or tip which is selected according the anatomy of the patient. For most human patients the length is preferably between about 1 inch and about 20 inches, and most typically between about 5.5 inches and about 6.5 inches. A number of specific length catheters can be made available as part of a kit so that the surgeon has a choice for a given situation. For example, a kit can contain six differently sized catheters ranging from 5 inches to 10 inches at 1 inch increments.

The balloon 307 is preferably formed from a highly resilient durable biocompatible material such as polyethylene terephthalate. It has a generally ellipsoidal shape when inflated and a generally cylindrical shape closely corresponding with the outer surface 308 of the distal segment 305 of the body 302 when deflated. The inflated diameter is selectable by the surgeon to be between the deflated diameter and a working inflated diameter of between about 2 mm to about 15 mm, typically about 7 mm, for use in the sinus system, except for use in the nasofrontal duct where the inflated working diameter is typically about 5 mm. The balloon has an axial length selected according the anatomy of the patient and the procedure being performed. For most uses a range of between about 2 mm and about 40 mm is preferred. Most typically the length can be about 14 mm.

A number of specific length balloons can be made available as part of a kit so that the surgeon has a choice for a given situation. For example, a kit can contain six differently sized balloons ranging from 3 mm to 15.5 mm at 2.5 mm increments. Alternately, a kit may contain balloons having different diameters from about 3 to 13 mm at 2.5 mm increments.

FIG. 1B shows that the balloon 307 has a distal neck 310, a distal tapered region 311, a center region 312, a proximal tapered region 313, and a proximal neck 314 and defines an internal chamber or inside 316 of the balloon. A layer of adhesive 315, such as cyanoacrylate, is used to bond the necks to the outer surface 308 of the body of the catheter.

The body comprises a plurality of conduits 320, 321, 322 to carry fluids to and from more distally located portions of the catheter. A plurality of conduits running through or bundled to form the body can be said to provide a multi-channel fluid buss through the catheter.

In most embodiments, the catheter should have sufficient stiffness and column strength with marked resistance to lateral bending that its distal segment carrying the deflated balloon can be used in the surgical methods described below, such as being pushed through a prepared small, tight opening from a sinus into the nose, pushed through a sinus ostium or duct, or pushed into a sinus cavity which may require considerable pressure in some cases. This required stiffness can be supplied by one or more of the conduits being formed from a rigid durable material such as stainless steel.

In the present embodiment the body has a pair of coaxial tubes 325,326, each having an opening or port 330,331 at the distal end 306 which is outside of the balloon and is located an axial distance $D_1$, $D_2$ from the distal neck 310 of the balloon 307. That distance is preferably between about 0 mm and about 5 mm, and is typically about 1 mm. The first external tube 325, is made from a rigid or semi-rigid durable material such as stainless steel, titanium and preferably supplies an irrigating fluid. The external irrigation tube preferably has an outer diameter which measures between about 0.05 inch and about 0.7 inch, and most typically about 0.095 inch. The inner diameter is preferably between about 0.020 inch and about 0.6 inch, and most typically about 0.071 inch.

The second, internal tube 326 runs through the central lumen of the external tube 325, thereby forming an annular conduit 322 between the tubes. The internal tube has its own central lumen which defines a second conduit 321 of the catheter which preferably provides suction. The internal tube can be made from thinner stainless steel or a more flexible material such as silicone or polyethylene. Care should be taken to select a material which has sufficient rigidity to prevent its collapse under the vacuum forces acting on the suctioned fluid. The internal suction conduit terminates at a nozzle 331 at the distal end 306 of the catheter. The irrigation conduit similarly terminates at the distal end forming an annular nozzle 330. The suction tube 326 has an outer diameter smaller than the inner diameter of the irrigation tube 325. The suction tube preferably has an outer diameter which measures between about 0.019 inch and about 0.59 inch, and most typically about 0.065 inch. The inner diameter is preferably between about 0.010 inch and about 0.58 inch, and most typically about 0.056 inch.

Referring now to FIGS. 1A and 1C, the proximal end 334 of the suction tube 326 extends a distance from the proximal end 335 of the irrigation tube 325 and terminates at a connector 336 allowing unobstructed connection to the suction source. The distance is preferably between about 0.5 centimeter ("cm") and about 5 cm, and most typically about 1 cm.

A third tube 340 is provided as a balloon inflation/deflation supply conduit, and extends substantially along the length of the body 302 and tangentially contacts the outer surface 337 of the first tube 325. It is made from thin stainless steel, flexible silicone, polyethylene or other durable, biocompatible material and has a central lumen defining a third conduit 320 of the catheter which terminates at an opening 339 inside the balloon. The third tube is preferably bonded to the first external tube by welding or an adhesive. This balloon supply conduit supplies fluid for filling and evacuating the balloon and is therefore in fluid communication with the inside 316 of the balloon. The inner diameter is preferably between about 0.005 inch and about 0.13 inch, and most typically about 0.020 inch. The outer diameter is preferably between about 0.015 inch and about 0.15 inch, and most typically about 0.028 inch. The proximal end 341 of the inflation/deflation supply tube 340 extends at an angle from the external irrigation tube and terminates at a connector allowing unobstructed connection to the balloon inflation/deflation fluid supply source. Alternately, the supply tube can remain straight and terminate at its proximal end luer lock connector a distance from the proximal end of the irrigation tube. The distance is preferably between about 1 millimeter ("mm") and about 10 cm, and most typically about 2 cm. The third inflation/deflation supply tube also extends at an angle away from the outer surface of the external tube which allows unobstructed connection to the balloon inflation/deflation supply.

Optionally, as shown in FIG. 1A, the catheter body may have axial gradations or other markings 309 which allow it to act as an axial measuring device to help ascertain or verify patient anatomy and location of the balloon.

Referring now to FIG. 1C, the proximal end 304 of the catheter 301 is formed to have connectors for each of the conduits. A first connector 336 on the suction conduit 321 can have wings 343 or other enlargement or expansion which are graspable by the surgeon to manipulate the catheter. The inner diameter of the connector 336 matches the external diameter of the suction hypotube 326 forming the suction conduit 321.

To supply the irrigation conduit 322, a small tube 344 extends at an angle through the sidewall of the irrigation conduit tube 325 and terminates in a connector 345 which connects to the irrigation sources. The length is preferably between about 1 millimeter ("mm") and about 50 mm, and most typically about 12 mm. The angle is preferably between about 1 degree and about 175 degree, and most typically about 45 degree. The inner diameter of the supply tube is preferably between about 0.010 inch and about 0.4 inch, and most typically about 0.070 inch. The outer diameter is preferably between about 0.020 inch and about 0.5 inch, and most typically about 0.083 inch.

A stopper 347 made from a resilient fluid impermeable material such as rubber seals the proximal end 335 of the external tube 325. The stopper has a central channel which allows passage of the suction tube 326 therethrough. The stopper may be sealed permanently using glue or other adhesive means or can be pressure fitted.

Because it is generally more important for the surgeon to more precisely control the location of the suction nozzle, the internal tube is used for suction. However, it is possible for the function of the first two conduits to be swapped.

Figure 2A:
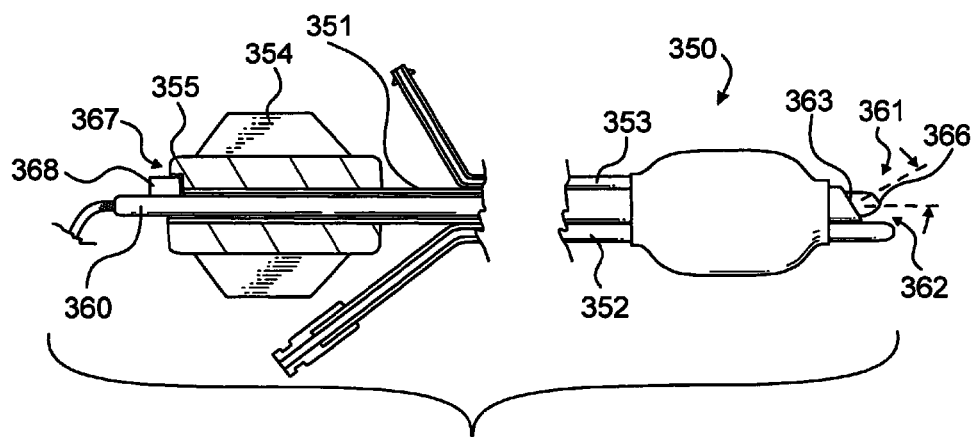
FIG. 2A is a closeup partial side elevational view and partial cross-sectional side view of the proximal and distal end segments of the suctioning and irrigating balloon catheter according to an alternate embodiment.

Referring now to FIG. 2A, there is shown an alternate embodiment of the suctioning and irrigating balloon catheter 350 having a first conduit 351 for carrying irrigation fluid, a second conduit 352 running along side the first conduit which provides suction and a third conduit 353 running along side the first conduit which inflates/deflates the balloon.

The irrigation conduit is fitted with hand manipulable wings 354 at it proximal end 355. The suction conduit is preferrably made from a durable rigid or semi-rigid material such as stainless steel or polyethylene. The inner diameter is preferably between about 0.012 inch and about 0.35 inch, and most typically about 0.05 inch. The outer diameter is preferably between about 0.025 inch and about 0.5 inch, and most typically about 0.065 inch.

The irrigation conduit can be utilized to carry an oblong endoscope 360 therethrough. The endoscope enables the surgeon to visualize the sinus cavity and associated structures.

Since many endoscopes have an angled view head 361 which can typically be at an angle of 30 degrees off the major axis of the endoscope, this embodiment provides a nozzle 362 at the distal end opening of the first irrigating conduit which has a cutaway 363 so as to not obscure the view from the distal tip of the endoscope. Further, in order to maintain the proper angular orientation of the endoscope head 366 with respect to the cutaway, an angularly keyed engagement 367 is provided at the proximal end of the catheter. In this way an endoscope having a correspondingly keyed haft in the form of a radial projection 368 will engage the engagement on a unique and appropriate angular orientation, thereby angularly securing the endoscope to the catheter. The radial projection also acts as an indicator of the angular orientation of the endoscope and catheter.

Figure 2B:
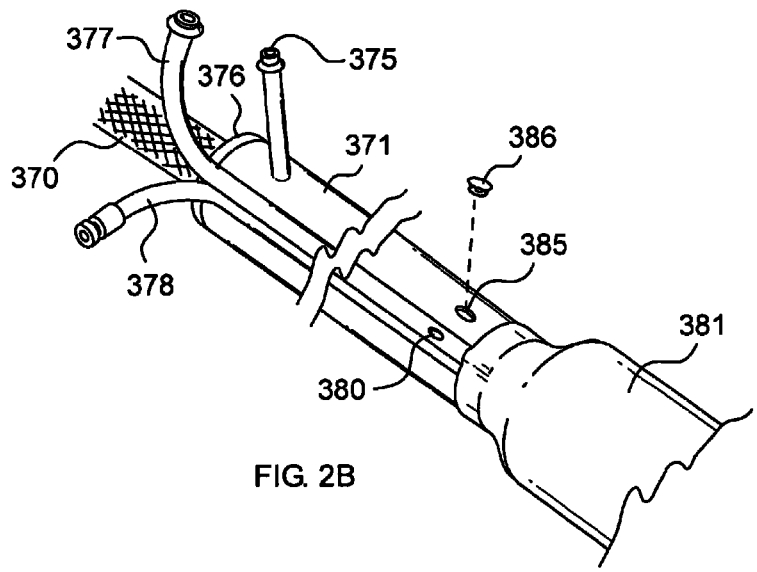
FIG. 2B is a closeup diagrammatic partial perspective view of the proximal end of a suctioning and irrigating balloon catheter according to another alternate embodiment.

FIG. 2B shows that the above embodiment can be adapted to provide an integrated endoscope 370 which is carried inside the first conduit 371. An external hypotube is selected to have an inner diameter which allows passage of an endoscope and provide enough space to form an annular conduit for carrying irrigation fluid. The inner diameter is preferably between about 0.02 inch and about 0.5 inch, and most typically about 0.1 inch. The outer diameter is preferably between about 0.03 inch and about 0.6 inch, and most typically about 0.134 inch.

A supply port 375 is provided to supply irrigating fluid which flows through the annular channel formed between the cylindrical outer surface of the endoscope 370 and the cylindrical inner surface of the first conduit 371. A stopper 376 prevents fluid from exiting the proximal end of the first conduit. A suction conduit 377 and balloon supply conduit 378 are formed onto the catheter body along side of the first conduit. Alternately, an additional suction port 380 is provided on the catheter body proximal to the balloon 381. The additional port is formed by a hole through the side wall of the suction conduit 377. In addition, irrigation proximal to the emplaced balloon can be provided by additional irrigation nozzles formed by one or more holes 385 through the outer hypotube wall of the irrigation conduit 371. Care should be taken to size the holes so that adequate suction and irrigation is provided at the distal terminus of the suction and irrigation conduits. Removable plugs 386 can be provided to seal off the additional holes when their use is not desired.

Figure 2C:
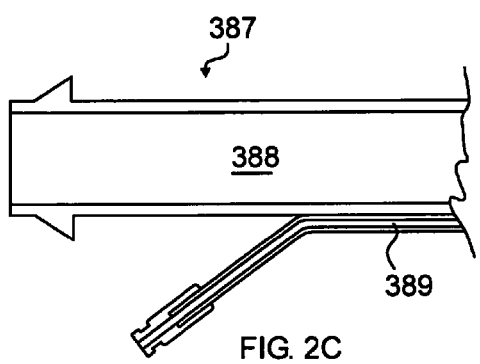
FIG. 2C is a closeup diagrammatic cross-sectional side view of the proximal end of a multi-conduit balloon catheter according to another alternate embodiment providing either suctioning or irrigating at one time.

As shown in FIG. 2C a multi-conduit balloon catheter 387 is provided having a first conduit 388 and a side-mounted inflation/deflation conduit 389. The first conduit can be used either for suctioning or irrigating, and can even be switched between suctioning and irrigating in-situ. Further, an endoscope can be inserted through the conduit.

Figure 2E:
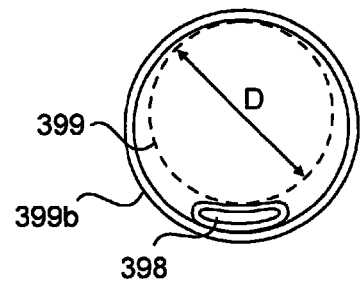
FIG. 2E is a diagrammatic cross-sectional end view of the a multi-conduit balloon catheter body having a flattened internal inflation/deflation conduit according to another alternate embodiment.
Figure 2D:
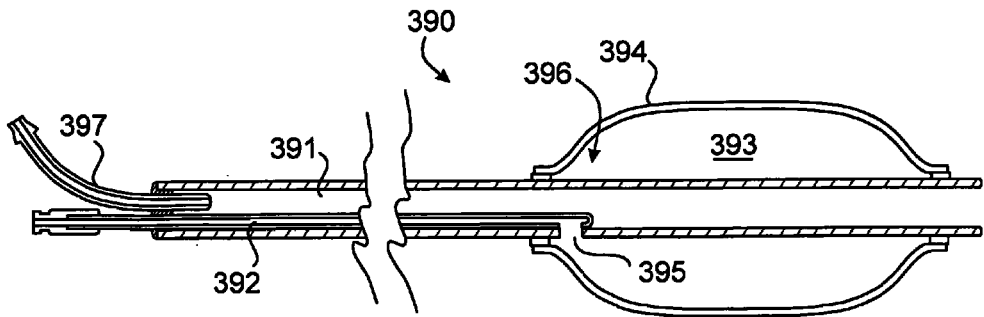
FIG. 2D is a closeup diagrammatic cross-sectional side view of the proximal and distal ends of a multi-conduit balloon catheter having an internal inflation/deflation conduit according to another alternate embodiment.

As shown in FIG. 2D, a multi-conduit balloon catheter 390 can have a first conduit 391 and a second, balloon inflation/deflation conduit 392 mounted internally within the first conduit. One way to allow the internal inflation/deflation conduit to be in fluid communication with the inside 393 of the balloon 394 is to provide a slot 395 extending through the side walls of the first an second conduit on a portion 396 of the catheter covered by the balloon. It should be noted that an engagement tube 397 is used for fluid communication with the inside of the first conduit. The first conduit can either be used for suction or irrigation and can be switched between the two in-situ.

As shown in FIG. 2E, the internal balloon inflation/deflation conduit 398 can be made to have a cross-section which is not circular, but rather is flattened in a generally rounded sickle shape in order to accommodate an endoscope 399 having a larger diameter D than would be available if the inflation/deflation conduit had a circular cross-section. In this way, the first conduit 399b can be kept small while still accommodating a larger diameter endoscope.

Figure 3A:
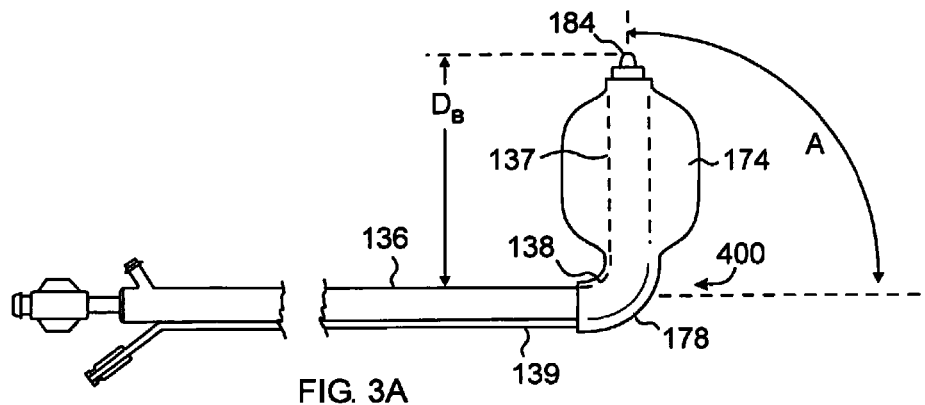
FIG. 3A is a diagrammatic elevational view of a suctioning and irrigating catheter having a distal bend.

As shown in FIG. 3A the catheter can be formed to have a bend 400 to allow more convenient and proper placement of the balloon during surgical procedures. The angle A formed by the bend is selected according the anatomy of the patient and the procedure being performed. Typically, the angle will be between 0 degrees (completely straight) and 130 degrees. There is a bend having a given radius which is preferably between about 0.05 inch and about 3 inches, and typically about 0.13 inch, and can be formed such that distal segment 137 is oriented 60 degrees to 130 degrees, preferably 90 degrees, to proximal segment 139. The axial distance $D_B$ from the distal tip 184 of distal segment 137 to the outer wall of proximal segment 139 of outer tube of the catheter 136 is 4 mm to 30 mm, preferably 14 mm. The proximal neck 178 may be bonded on distal segment 137 of tube 136 or extend over bend 138 onto the distal end portion of proximal segment 139 of tube 136. Extension of the proximal neck 178 onto bend 138 and proximal segment 139 allows a greater length of the working diameter, i.e., center region 174, to be on distal segment 137 of tube 136.

The length of the distal segment is short enough to allow it to be rotated within the nasal cavity and thus enter from the nasal cavity into the sinus at the desired angle. The distal segment is long enough to allow a balloon of sufficient length and diameter to be attached for dilation of an opening through the lateral nasal and sinus wall, duct, ostium or choana. The balloon material is attached with adhesive to the very distal portion of the distal segment and to the proximal portion of the distal segment, the bend, and the very distal portion of the proximal segment. A longer working segment of balloon can be used because the area of adhesion of the balloon includes the bend and the distal portion of the proximal segment. A 7 mm inflated diameter angled balloon is used to treat the maxillary sinus and a 5 mm inflated diameter angled balloon is to treat the frontal sinus. The balloon diameter can vary from about 2 to 20 mm in diameter.

Figure 3B:
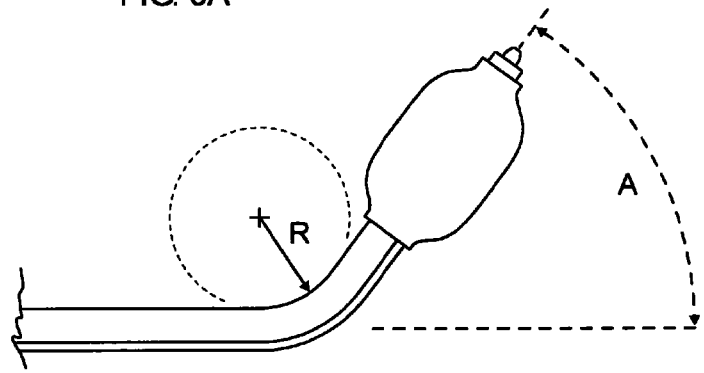
FIG. 3B is a diagrammatic partial side elevational view of the suctioning and irrigating balloon catheter being bent with a given radius.

The catheter is formed to have sufficient stiffness and column strength to be pushed through a surgically prepared small, tight opening from the sinus into the nose, through a sinus or osteum or duct, or into a sinus cavity, or into the choana. Therefore, at least one of the tubes, and preferably the largest outer tube is formed from a hypotube of stainless steel or other rigid or semi-rigid, durable, biocompatible material. However, it can also be advantageous to form the catheter such that it has a stiffness which allows it to be hand bent by the surgeon prior to or even during surgery. This stiffness tradeoff can lead to a catheter which is difficult to bend properly so as not to create kinks in one or more of the conduits, and which is essentially hand unbendable. A type of steel having a higher malleability can be used which can allow sharper bending without kinking. In addition, most commercially available flexible endoscopes are not intended to be bent further than a minimum radius. In other words, bends in the flexible body of the endoscope should not be sharper than a minimum radius. Therefore, as shown in FIG. 3B, the surgeon should take care not to bend the bendable catheter to have a curve sharper than a given radius R.

Figure 3C:
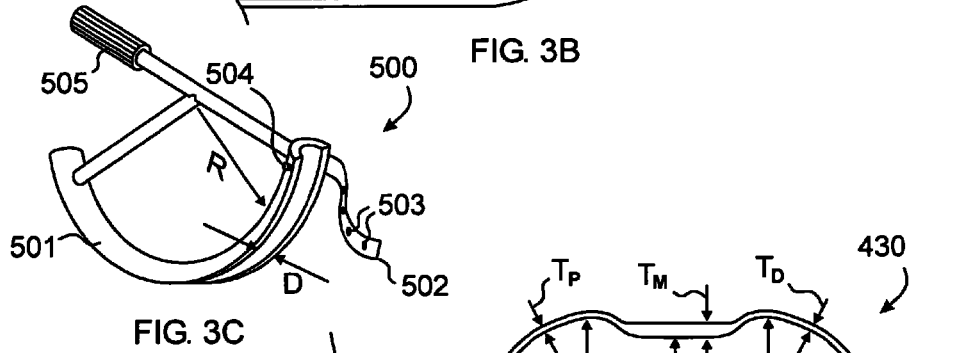
FIG. 3C is a diagrammatic perspective view of a tool for bending a catheter according to a given radius.

As shown in FIG. 3C, as part of the kit, the surgeon is provided with a manual bending tool 500 similar to a pipe bending tool used by plumbers. The tool has a rigid, arcuate contact plate 501 in a generally half-pipe shape having a lateral diameter D which is commensurate with the outer surface diameter of the catheter body. This provides the tool with a first surface which can intimately contact and bear against a portion of the catheter body proximate to the axial location of the intended bend. The plate is also curved longitudinally to have a given radius R. A releasably adjustable strap 502 is provided for temporarily fastening a portion of the catheter body to the tool. The strap has a number of button holes 503 for engaging a button 504 on the tool to accommodate a range of catheter body outer diameters. A handle 505 provides for manual control of the tool by the surgeon. In this way the surgeon can precisely shape the catheter, even during surgery if necessary, to have one or more bends of a given bend radius R. If a flexible endoscope is to be treaded through the catheter, the given bend radius should be greater than or equal to the minimum bend radius of the endoscope. For many applications the preferred bend radius is at least 0.5 centimeter. Further, tools having different radiuses can be supplied in the kit. Further the surgeon can form bends outside the plane of prior bends, thereby making a custom three dimensional rigid catheter for a given patient and procedure.

Figure 3D:
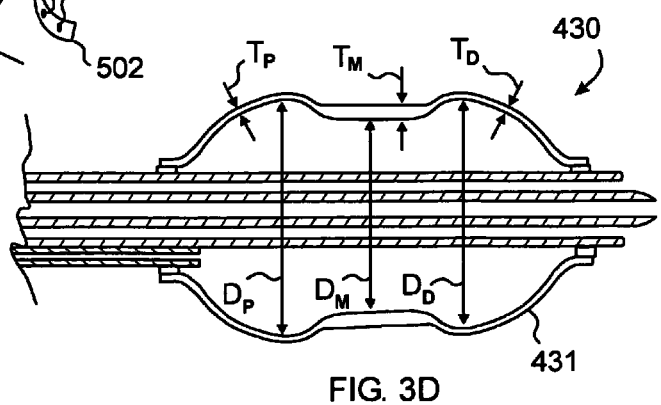
FIG. 3D is a closeup diagrammatic cross-section view of the distal end segment of the suctioning and irrigating balloon catheter according to another alternate embodiment having a pinched center balloon.

Referring now to FIG. 3D, there is shown an alternate embodiment of the suctioning and irrigating catheter 430 having a balloon 431 which, when inflated, has a diameter in a medial section $D_M$ which is smaller than the diameter on adjacent proximal $D_P$ and distal sections $D_D$. This allows the tissue/balloon interface to have greater axial stability during inflation. The substantially barbell shaped balloon can be formed a number of ways. The preferred approach provides an axially medial section of the balloon having a relatively greater thickness $T_M$ than the thickness of adjacent proximal $T_P$ and distal $T_D$ sections. The thickness of the proximal and distal sections is preferably between about 0.0001 inch and about 0.1 inch, and most typically about 0.002 inch. The thickness of the medial section is preferably between about 0.0001 inch and about 0.1 inch, and most typically about 0.004 inch.

Referring now to FIGS. 3E and 3F, there is shown an alternate embodiment of the suctioning and irrigating catheter 530 having a balloon 531 mounted upon the distal end segment 532 of a body 533 made from a durable, biocompatible, flexible material such as polyethylene or high malleability steel. The catheter has a first, inflation/deflation supply tube 534 for operating the balloon, and a second, suctioning tube 535 terminating at a distal suctioning port 536 located distally from the balloon. The flexible body catheter also has a third tube 537 shaped and dimension to be fitted as a sheath over an oblong, rigid, rod-like, rigidizing member 538 having a blunted distal end 539. The sheath has an open proximal end 540 and a constricted, small diameter opening or nozzle 541 at a distal end 543 and a central lumen having an inner diameter slightly larger than the outer diameter 542 of the rigidizing member. Once the body is fitted over the rigidizing member, the catheter has sufficient stiffness and column strength to allow it to be pushed into the intended space in the patient. Once emplaced and the rigidizing member can be withdrawn leaving the flexible body to more comfortably conform to the patients internal anatomy.

It should be noted that the nozzle 541 is sized to prevent passage of the rigidizing member therethrough but does allow the sheath to also act as a fluid conduit for irrigation and/or suctioning purposes once the rigidizing member is removed. Alternately, the distal end 543 of the sheath can be completely sealed off. Alternately, the rigidizing member can be hollow such as in the form of a hypotube, or otherwise shaped to allow for passage of fluid through the open distal ended sheath while the rigidizing member is inserted.

Referring now to FIGS. 3G-3I, there are shown differently shaped rigidizing members. In FIG. 3G the rigidizing member 550 is shaped to have a bend 551 which orients a distal portion 552 at an angle $A_R$ to a proximal portion 553 of the member proximal to the bend. The member in FIG. 3F shows an angle $A_R$ of about 0 degrees. The member in FIG. 3G shows an angle $A_R$ of about 60 degrees. The member in FIG. 3H shows an angle $A_R$ of about 90 degrees. The member in FIG. 3I shows an angle $A_R$ of about 130 degrees.

As will be described below, an angled suctioning and irrigating catheter 130 and a "straight" suctioning and irrigating catheter 230 can be used in different method steps for treating various prepared openings, naturally occurring ostia and ducts, choana, and sinus cavities. Depending on the size of the anatomical structures and the procedure being performed, the surgeon may also decide whether to utilize a suctioning and irrigating balloon catheter having an integrated endoscope. It is also to be noted that dimensions of the catheters are selected to accommodate different conditions in the paranasal sinus system. For example, the outer diameters of the distal segments with the balloon deflated are selected so that the respective distal segments with the balloon deflated will fit snugly with the prepared openings, natural ostia or ducts, choana and sinus cavities into which these distal segments are to be pushed. As already mentioned, the working inflated diameters of the balloons differ depending on the size required to treat different parts of the paranasal sinus system. Accordingly, the surgeon can, at the time surgery is begun, have available a set of sinus balloon catheters which are angled or straight, the balloons of which have appropriate inflated working diameters, and which have appropriate outer diameters with the balloon deflated that will enable the catheter in question to be pushed into the respective prepared opening, natural ostium or duct or sinus cavity to be excised.

It is also useful to apply a lubricious coating to the balloon material to facilitate pushing it through the lateral nasal wall and sinus wall into the sinus.

Figure 4:
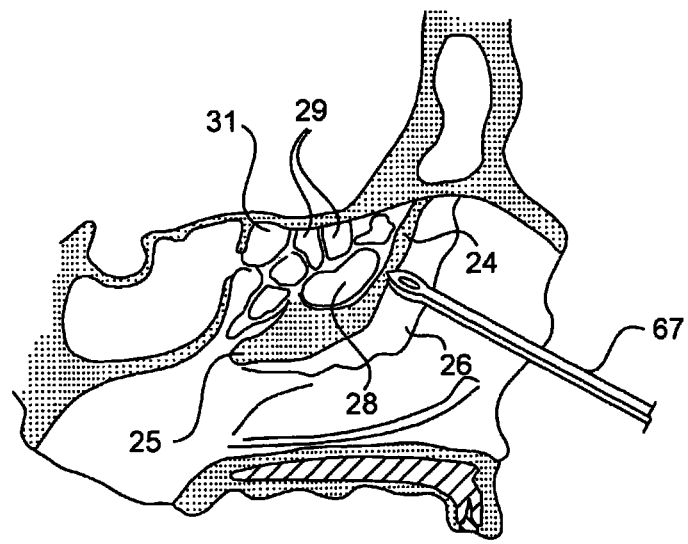
FIG. 4 is a schematic drawing of a step of a method, showing the uncinate process being removed with a punch to expose the ethmoid infundibulum and semilunar hiatus.
Figure 5:
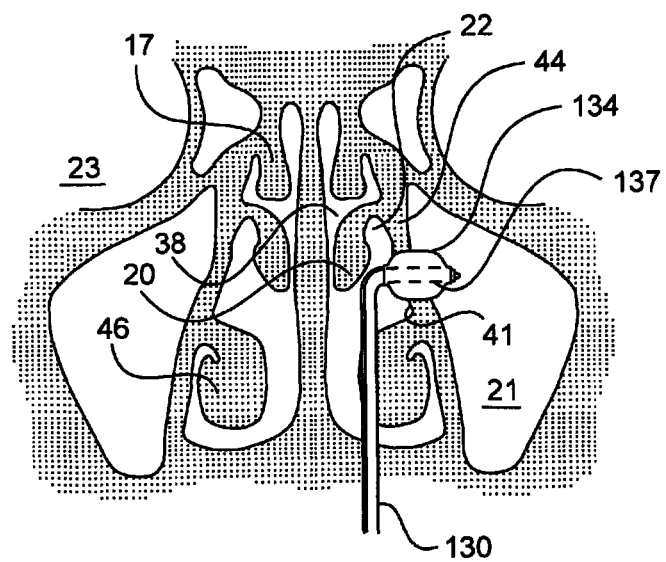
FIG. 5 is a schematic drawing of another step of the method of FIG. 4 showing the sinus balloon catheter dilating and thereby enlarging the ostium of the maxillary sinus and performing suction and irrigation functions.

Turning to FIGS. 4 and 5, in a method of performing balloon catheter antrostomy of the maxillary ostium, the middle turbinate 20 is retracted medially to gain access to the middle meatus 22. In some cases the middle turbinate is resected. The ethmoid infundibulum 24 is exposed by using cutting forceps 67 to remove part of the uncinate process 26 (FIG. 4). Distal segment 137 of balloon catheter 130 is then pushed through the maxillary ostium 41 (which is in ethmoid infundibulum 24) into the maxillary sinus 21. In some cases however, the maxillary ostium can be entered by the balloon catheter without removal of the uncinate process. As seen in FIG. 5, balloon 134 is inflated to between about 1 and 17 bars, and most typically about 9 bars (atmospheres) for between about 1 second and 20 minutes, and most typically about 20 seconds then deflated. Distal segment 137 of balloon catheter 130 is slightly repositioned to insure full dilation and inflated again to 9 bars for 20 seconds. Balloon 134 is then deflated, and catheter 130 is removed from the now enlarged ostium 41. The irrigation and suction functions of the catheter are used to irrigate off and suction away blood, pus and other debris from the surrounding tissues, while the endoscope function provides good visualization for the surgeon. In this way, the surgeon does not need to hold a separate suction catheter and an irrigating cannula in addition to the endoscope.

Figure 6:
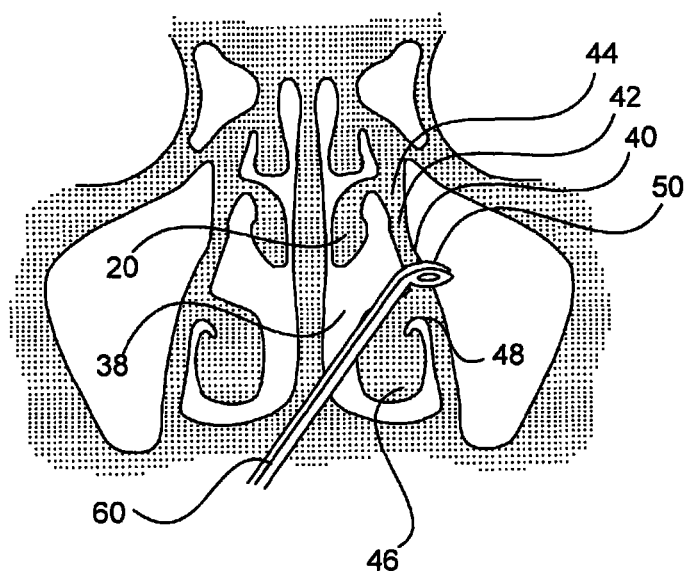
FIG. 6 is a schematic drawing of a step of a second method showing the Blakesely punch creating a small opening in the fontanelle of the lateral nasal wall in the middle meatus thus creating a communication between the maxillary sinus and nasal cavity.
Figure 7:
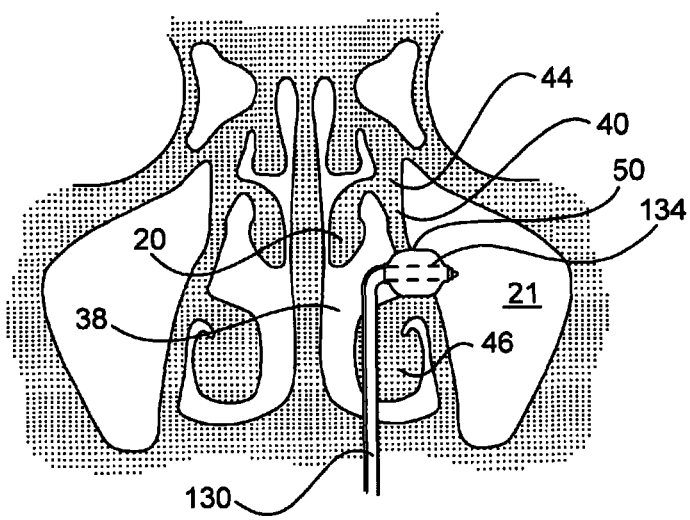
FIG. 7 is a schematic drawing of another step of the method of FIG. 6 showing the sinus balloon catheter dilating the opening in the fontanelle of the lateral nasal wall in the middle meatus thus creating a large communication opening (antrostomy) for drainage from the maxillary sinus into the nasal cavity and performing suction and irrigation functions.

Turning to FIGS. 6 and 7, in a method of performing a middle meatal maxillary antrostomy, an initial opening is made in the fontanelle 40 (section of thin membranous tissue without bone of the medial maxillary sinus wall 42 which is also a portion of the lateral nasal wall 44). This is performed by bringing a 45 degree upbiting Blakesely punch 60 into nasal cavity 38 along the lateral nasal wall 44 just superior to the inferior turbinate 46 at the midpoint of its horizontal axis to perforate fontanelle 40 to create a new 3 mm opening 50 (FIG. 6). The punch 60 is removed, and sinus balloon catheter 130 is brought into nasal cavity 38 and pushed into the new opening 50 in fontanelle 40 of lateral nasal wall 44 (FIG. 7). Balloon 134 is inflated to 9 bars for 20 seconds then deflated. Balloon catheter 130 is slightly repositioned in the enlarged opening 50 to insure thorough dilation and inflated again to 9 bars for 20 seconds. Balloon catheter 130 is then deflated and withdrawn from opening 50 and nasal cavity 38. The irrigation and suction functions of the catheter are used to irrigate off and suction away blood, pus and other debris from the surrounding tissues, while the endoscope function provides good visualization for the surgeon.

Figure 8:
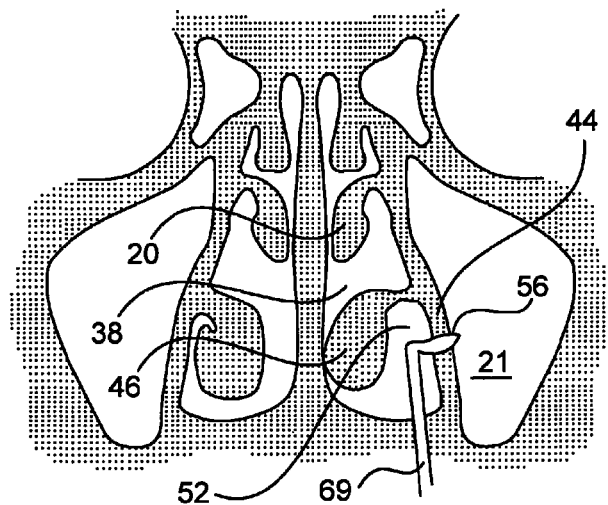
FIG. 8 is a schematic drawing of a step of a third method showing the dissector perforating the lateral nasal wall in the inferior meatus into the maxillary sinus.
Figure 9:
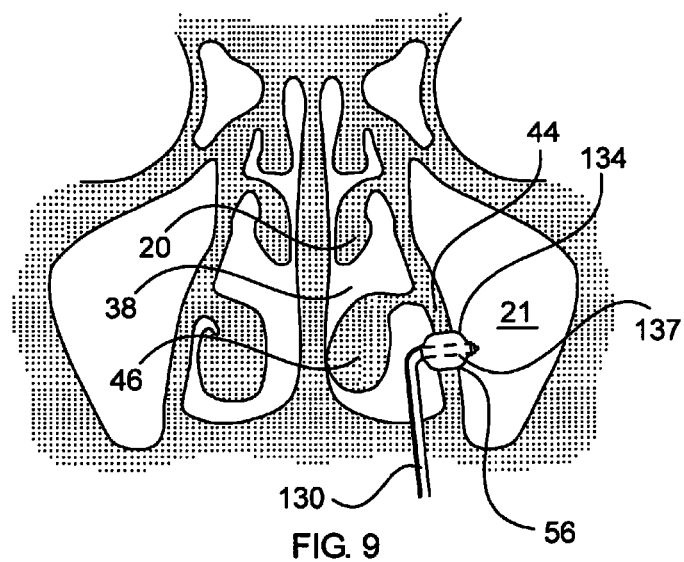
FIG. 9 is a schematic drawing of another step of the method of FIG. 8 showing the sinus balloon catheter dilating the opening in the lateral nasal wall in the inferior meatus thus creating a large antrostomy for drainage from the maxillary sinus into the nasal cavity and performing suction and irrigation functions.

As seen in FIGS. 8 and 9, in a method of inferior meatal antrostomy, the inferior turbinate 46 has been displaced medially. A sharp dissector 64 is introduced into nasal cavity 38 and used to perforate lateral nasal wall 44 in the inferior meatus 52 to create an opening 56 in lateral nasal wall 44 (FIG. 8). Dissector 64 is withdrawn from nasal cavity 38. The deflated balloon catheter 130 is introduced into the nasal cavity 38, and distal segment 137 of balloon catheter 130 is pushed through opening 56 in lateral nasal wall 44. The balloon 134 is inflated to 9 bars for 20 seconds then deflated. Deflated balloon 134 is slightly repositioned to assure total dilation of the opening 56. A second dilation of the balloon 134 to a pressure of 9 bars for 20 seconds is performed. The balloon catheter 130 is then deflated and withdrawn from opening 56 and nasal cavity 38. The irrigation and suction functions of the catheter are used to irrigate off and suction away blood, pus and other debris from the surrounding tissues, while the endoscope function provides good visualization for the surgeon.

Figure 10:
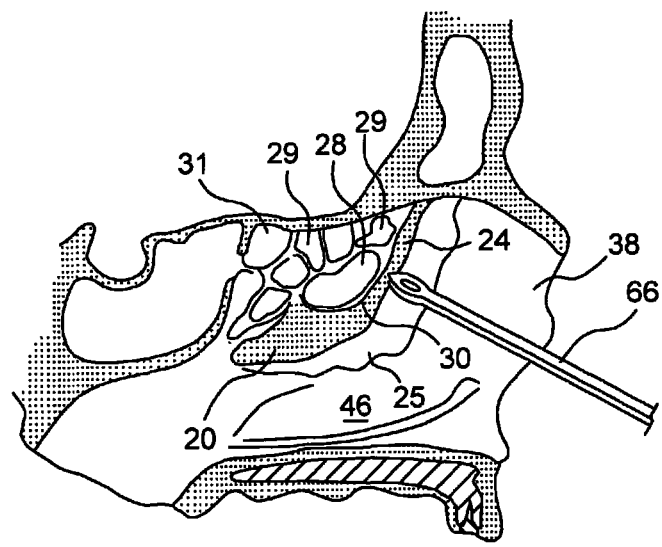
FIG. 10 is a schematic view of a fourth method showing the cutting forceps making a new opening in the anterior wall of the ethmoid bulla.
Figure 11:
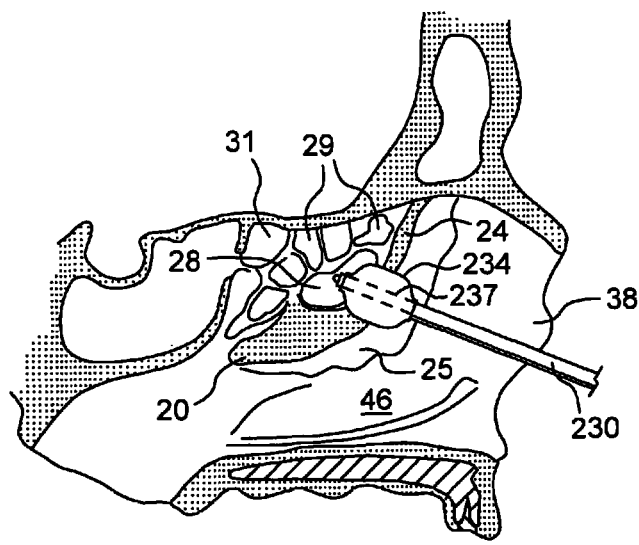
FIG. 11 is a schematic view of another step of the method of FIG. 10 showing the straight sinus balloon catheter dilating the ethmoid bulla and performing suction and irrigation functions.
Figure 12:
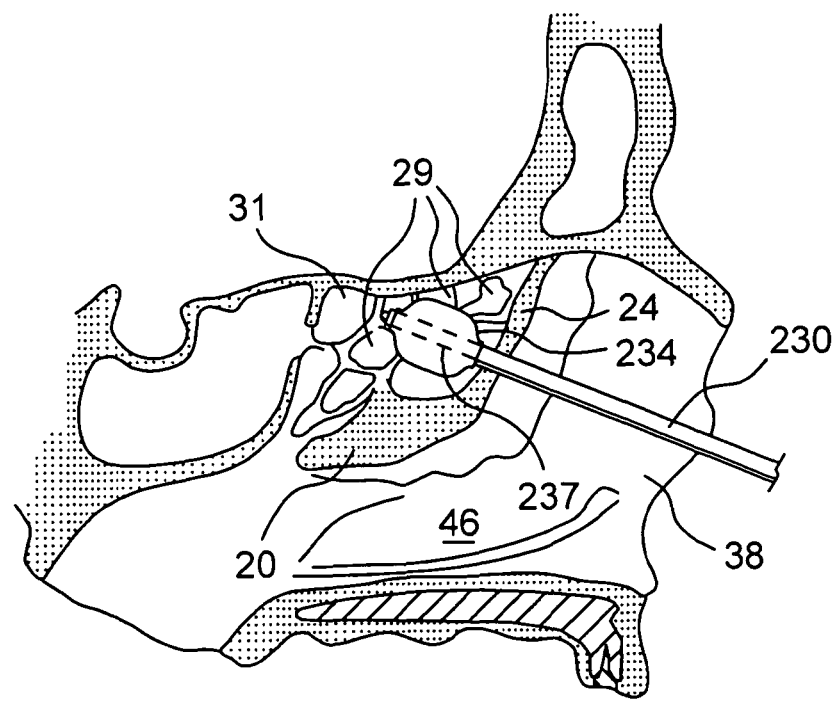
FIG. 12 is a schematic view of yet another step of the method of FIG. 10 showing the straight sinus balloon catheter dilating the ethmoid air cells and thus completing the anterior ethmoidectomy and performing suction and irrigation functions.

A balloon catheter ethmoidectomy of the anterior ethmoid sinus is shown in FIGS. 10-12. The middle turbinate 20 (FIG. 5) has been retracted medially to gain access to the middle meatus 22 (FIG. 5). In some cases, the middle turbinate may be partially or totally removed. The ethmoid infundibulum 24 is exposed by removing part of the uncinate process 26 (FIG. 4). A fine cutting forceps 66 is used to remove the anterior wall 30 of the ethmoid bulla 28 (FIG. 10). After anterior wall 30 of ethmoid bulla 28 is removed, the straight balloon catheter 230 is brought into nasal cavity 38, and distal segment 237 is pushed into bulla 28 (FIG. 11). In some cases, the catheter can be pushed directly into the sinus without removing the anterior wall or the uncinate process. The irrigation and suction functions of the catheter are used to irrigate off and suction away blood, pus, a mucocele, if present, and other debris from the surrounding tissues and endoscope, while the endoscope function provides good visualization for the surgeon. The balloon 234 is inflated to 9 bars for 20 seconds then deflated. The catheter 230 is then withdrawn from bulla 28. The distal segment 237 of balloon catheter 230 is then pushed into the anterior ethmoid air cells 29 which lie posterior to the previously removed ethmoid bulla 28 (FIG. 12). The balloon 234 is inflated to 9 bars for 20 seconds then deflated. Balloon catheter 230 is then slightly repositioned to insure thorough dilation and inflated again to 9 bars for 20 seconds, deflated, and removed from the area of anterior ethmoid cells 29. Again the irrigation and suction functions of the catheter are used to irrigate off and suction away blood, pus, a mucocele, if present, and other debris from the relevant structures, while the endoscope function provides good visualization for the surgeon.

Figure 13:
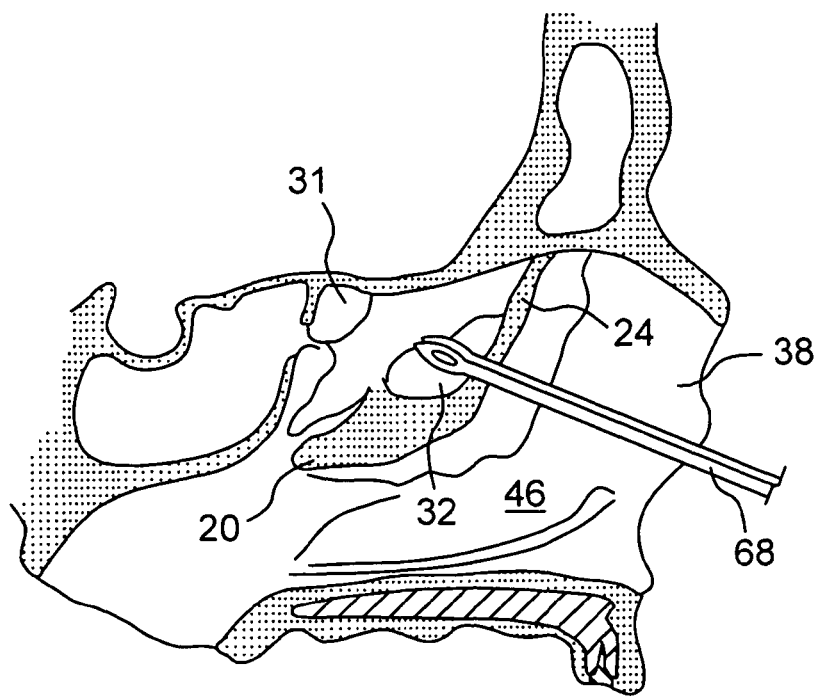
FIG. 13 is a schematic view of yet another step of the method of FIG. 10 showing a punch perforating the basal lamella of the middle turbinate.
Figure 14:
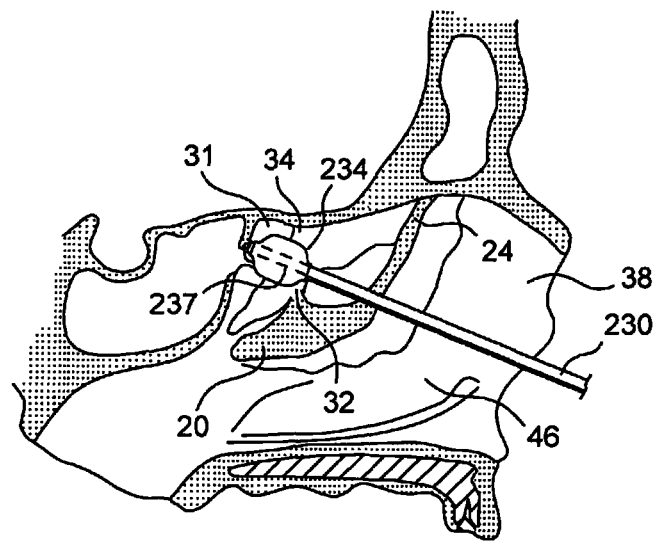
FIG. 14 is a schematic view of still another step of the method of FIG. 10 showing the straight sinus balloon catheter dilating the posterior ethmoid air cells and thus completing the posterior ethmoidectomy and performing suction and irrigation functions.

FIGS. 13 and 14 illustrate an ethmoidectomy of the posterior ethmoid sinus. When the posterior ethmoid sinus cells 31 must be removed, the basal lamella 32 of the middle turbinate 20 is perforated with a punch 68 (FIG. 13). Distal segment 237 of balloon catheter 230 is then pushed through the new opening 34 in the basal lamella 32 of the middle turbinate 20 into the posterior ethmoid air cells 31 and inflated 9 bars for 20 seconds (FIG. 14). In some cases the catheter may be pushed directly into the posterior ethmoid sinus without first perforating with a punch. The balloon catheter 230 is then deflated, slightly repositioned, and again inflated 9 bars for 20 seconds. The balloon catheter 230 is then deflated and withdrawn. The irrigation and suction functions of the catheter are used to irrigate off and suction away blood, pus, a mucocele, if present, and other debris from the surrounding tissues, while the endoscope function provides good visualization for the surgeon.

Figure 15:
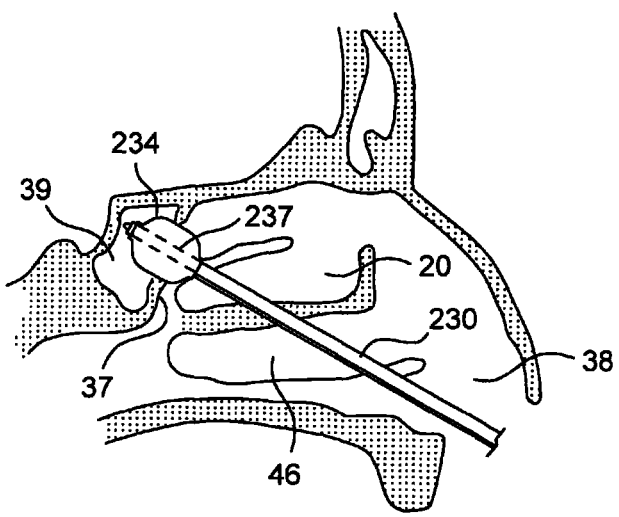
FIG. 15 is a schematic view of an additional step of the method of FIG. 10 showing the sinus balloon catheter dilating the anterior wall of the sphenoid sinus and performing suction and irrigation functions.

FIG. 15 shows sinusotomy of the sphenoid sinus. After anterior and posterior ethmoidectomy, distal segment 237 of balloon catheter 230 is inserted through the anterior wall 37 of sphenoid sinus 39 (FIG. 15). In some cases the catheter can be placed in the sphenoid sinus without first performing an ethmoidectomy. The balloon 234 is then inflated to 9 bars for 20 seconds then deflated. The balloon catheter 230 is slightly repositioned to insure thorough dilation and inflated again to 9 bars for 20 seconds, then deflated, and withdrawn. The irrigation and suction functions of the catheter are used to irrigate off and suction away blood, pus, a mucocele, if present, and other debris from the relevant structures, while the endoscope function provides good visualization for the surgeon.

Figure 16:
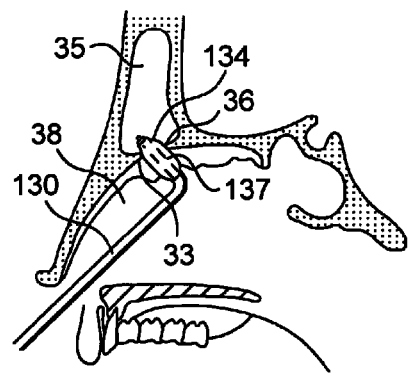
FIG. 16 if a schematic view of a further step of the method of FIG. 10 showing the angled sinus balloon catheter dilating the frontonasal duct and performing suction and irrigation functions.

FIG. 16 illustrates sinusotomy of the frontal sinus. After an anterior ethmoidectomy the nasofrontal duct 36 is exposed and in the surgeon's view. The distal segment 137 of an angled catheter 130 with a 5 mm inflated working diameter is brought into the frontonasal duct 36 and inflated to 9 bars, then deflated. In some cases the catheter can be placed into the frontonasal duct and sinus without first performing an ethmoidectomy. The distal segment 137 of the balloon catheter 130 is slightly repositioned to insure complete dilation of the nasofrontal duct 36 and inflated to 9 bars for 20 seconds then deflated and withdrawn. The irrigation and suction functions of the catheter are used to irrigate off and suction away blood, pus, a mucocele, if present, and other debris from the surrounding tissues, while the endoscope function provides good visualization for the surgeon.

Figure 17:
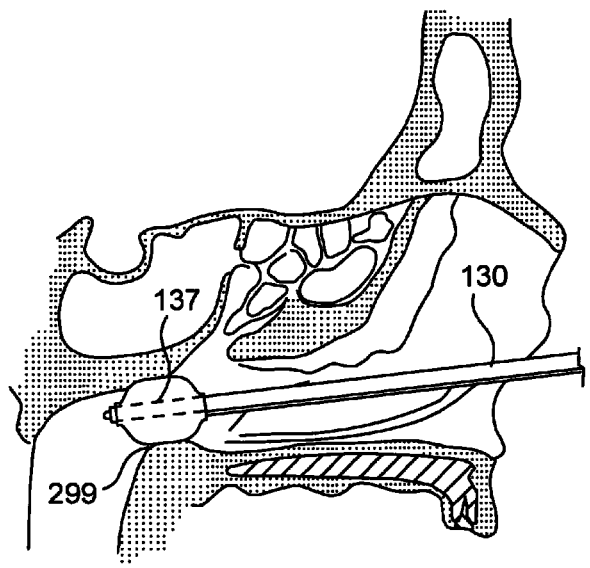
FIG. 17 is a schematic drawing of a step of a method showing the suctioning and irrigating balloon catheter dilating the choana and performing suction and irrigation functions.

FIG. 17 illustrates balloon catheter dilation of the choana, the posterior opening to the nasal cavity. This procedure can be useful for treating choanal stenosis (narrowing of the choana), and choanal atresia. The distal segment 137 of the balloon catheter 130 is positioned in the choana 299 and inflated to 8 bars for 30 seconds then deflated and withdrawn. The irrigation and suction functions of the catheter are used to irrigate off and suction away blood, pus and other debris from the surrounding tissues, while the endoscope function provides good visualization for the surgeon.

All of the above procedures may be performed in a similar fashion in patients who have had previous sinus surgery and the sinus openings have been obstructed by scar tissue or granulation tissue.

While the preferred embodiment of the invention has been described, modifications can be made and other embodiments may be devised without departing from the spirit of the invention and the scope of the appended claims.

What is claimed is:

1. A method of treating a patient's nasal sinuses using a balloon catheter, wherein the balloon catheter comprises an oblong body, a first tube, a second tube, and a third tube, wherein the oblong body has a proximal segment and a distal segment, wherein the oblong body further has an expandable balloon located on the distal segment, wherein the first tube comprises a first lumen having a first flow path, wherein the first lumen terminates at a first port distal to the balloon, wherein the second tube is disposed about the first tube such that a second lumen having a second flow path is defined between an exterior surface of the first tube and an interior surface of the second tube, wherein the second tube terminates at a second port distal to the balloon, wherein the third tube is laterally offset from the first and second tubes such that an exterior surface of the third tube tangentially contacts an exterior surface of the second tube, wherein the third tube comprises a third lumen having a third flow path, wherein the third tube terminates at a third port within the balloon, the method comprising:
(a) inserting an endoscope into the first tube, through the first lumen of the first tube, such that a distal end of said endoscope protrudes from said first tube, wherein the first tube comprises a distal nozzle, wherein the distal end of the said endoscope is aligned with an obliquely angled cutaway on the distal nozzle of the first tube;
(b) pushing the distal segment into a space associated with a nasal sinus of said patient, wherein the balloon is in a deflated state during the act of pushing the distal segment;
(c) inflating the balloon to dilate the space, wherein the act of inflating the balloon comprises communicating fluid through the third flow path and through the third port into the balloon;
(d) irrigating the space, wherein the act of irrigating the space comprises communicating fluid through the first flow path of the first lumen of the first tube and through the first port into the space via the distal nozzle; and
(e) suctioning fluid and material from the space, wherein the act of suctioning fluid and material from the space comprises communicating suction through the second flow path and through the second port into the space.

2. The method of claim 1, wherein said space is formed in the patient's ethmoid bulla.

3. The method of claim 1, wherein said space is an opening through the patient's anterior wall of the patient's sphenoid sinus; and wherein said method further comprises deflating said balloon and removing said distal segment to complete sinusotomy of said sphenoid sinus.

4. The method of claim 1, wherein said space is the patient's nasofrontal duct to the patient's frontal sinus; and wherein said method further comprises deflating said balloon and removing said distal segment to complete sinusotomy of said frontal sinus.

5. The method of claim 1, wherein said space is a choana, said distal segment with said balloon deflated being pushed into the choana, said choana being dilated when said inflatable member is inflated.

6. The method of claim 1, wherein said space is a prepared opening formed through the patient's lateral nasal wall in the patient's inferior meatus.

7. The method of claim 6, wherein prepared opening is formed by displacing the patient's inferior turbinate medially, introducing a sharp dissector into the patient's nasal cavity, and using said dissector to perforate the patient's lateral nasal wall in said inferior meatus to form said opening and wherein said distal segment with said balloon deflated is pushed into said prepared opening and said balloon is inflated to dilate said prepared opening.

8. The method of claim 7, which further comprises:
(a) medially retracting the patient's middle turbinate to gain access to the patient's middle meatus;
(b) exposing the patient's ethmoid infundibulum by removing part of the patient's uncinate process; and,
(c) using a fine cutting forceps to remove the anterior wall of said ethmoid bulla.

9. The method of claim 8, wherein after said inflatable balloon is deflated and withdrawn from said ethmoid bulla, providing said opening in said ethmoid bulla to receive said distal segment, which when inflated, dilates and thereby removes said ethmoid bulla.

10. The method of claim 9, wherein said inflated balloon is then deflated and said distal segment is then withdrawn from the space formerly occupied by said ethmoid bulla, said distal segment with said balloon deflated is then pushed into the patient's anterior ethmoid air cells, forming the patient's ethmoid sinus, lying posterior to said space formerly occupied by said ethmoid bulla, said balloon is then inflated dilating said anterior ethmoid air cells and thereby removing said anterior ethmoid air cells, and said balloon is then deflated, and said distal segment is then removed from the space formerly occupied by said anterior ethmoid air cells, completing an ethmoidectomy of the anterior ethmoid sinus.

11. The method of claim 10, wherein the patient's basal lamella of the patient's middle turbinate is perforated with a punch to form an opening, said distal segment is then pushed through said opening into said posterior ethmoid air cells and said balloon is inflated to dilate and remove said posterior ethmoid cells completing an ethmoidectomy of said posterior ethmoid sinus.

12. The method of claim 11, wherein after said anterior and posterior ethmoidectomies are completed, inserting said distal segment through the patient's anterior wall of the patient's sphenoid sinus, the balloon is then inflated for dilation and opening of said sphenoid sinus, the deflating said balloon and removing said distal segment to complete sinusotomy of said sphenoid sinus.

13. The method of claim 11, wherein after said ethmoidectomy of said anterior ethmoid sinus is completed and the patient's nasofrontal duct is exposed, providing a second balloon catheter having a tubular catheter body with a proximal segment, a distal segment, a balloon member mounted around said distal segment, a slot through the wall of said distal segment, said tubular body being closed at a point distally of said slot, and means providing fluid under pressure at the proximal end of said tubular catheter body to inflate said balloon, said tubular catheter body having a bend placing said distal segment at an angle of between about 60 degrees and about 130 degrees to said proximal segment, pushing said distal segment of said second balloon catheter with said balloon of said second balloon catheter deflated into said frontonasal duct, inflating second balloon catheter to dilate said frontonasal duct and frontal sinus, deflating said balloon of said second balloon catheter, and removing said distal segment of said second balloon catheter to complete a frontal sinusotomy.

14. A method of treating a patient's nasal sinuses, comprising:
(a) providing a balloon catheter having:
(i) an oblong body having a proximal segment and a distal segment, an expandable balloon located on said distal segment, and,
(ii) a first conduit having a first distal nozzle, wherein an endoscope locking feature is formed in a wall of the first conduit, wherein the endoscope locking feature is configured to ensure proper alignment of an endoscope;
(b) inserting said endoscope in said first conduit such that a distal end of said endoscope protrudes from said first distal nozzle, and orienting said endoscope such that a projection of said endoscope engages said endoscope locking feature formed in said wall of said first conduit;
(c) pushing said distal segment with said balloon deflated into a space associated with a nasal sinus of said patient;
(d) viewing said space by way of said endoscope;
(e) irrigating said space through said first conduit; and,
(f) inflating said balloon to dilate said space.

15. The method of claim 14, wherein said space is a prepared opening formed through the patient's fontanelle, said opening is formed by bringing a 45 degree upbiting Blakesely punch into the patient's nasal cavity along the patient's lateral nasal wall just superior to the patient's inferior turbinate, pushing said punch through said fontanelle to create said opening through said fontanelle and wherein said distal segment with said balloon deflated is pushed into said prepared opening and said balloon is inflated to dilate said prepared opening.

16. A method of treating a patient's nasal sinuses using a balloon catheter, wherein the balloon catheter comprises an oblong body, a first lumen, a second lumen, and a third lumen, wherein the oblong body has a proximal segment and a distal segment, wherein the oblong body further has an expandable balloon located on the distal segment, wherein the first lumen defines a first flow path, wherein the first lumen terminates at a first port distal to the balloon, wherein the second lumen is disposed about the first lumen such that a second flow path is defined between an exterior of the first lumen and an interior of the second lumen, wherein the second lumen terminates at a second port distal to the balloon, wherein the third lumen is laterally offset from the first and second lumens, wherein the third lumen defines a third flow path, wherein the third lumen terminates at a third port within the balloon, the method comprising:

(a) inserting a rigidizing member into the first lumen, wherein the first lumen defines a nozzle on a distal end of the first lumen such that the nozzle prevents the rigidizing member from protruding through the nozzle;

(c) pushing the distal segment into a space associated with a nasal sinus of said patient, wherein the balloon is in a deflated state during the act of pushing the distal segment;

(d) inflating the balloon to dilate the space, wherein the act of inflating the balloon comprises communicating fluid through the third flow path and through the third port into the balloon; and (e) suctioning fluid and material from the space, wherein the act of suctioning fluid and material from the space comprises communicating suction through the second flow path and through the second port into the space;

wherein the space is selected from the group consisting of a prepared opening formed through the patient's lateral nasal wall in the patient's inferior meatus, a prepared opening formed in the patient's ethmoid bulla; an opening through the patient's anterior wall of the patient's sphenoid sinus;

an opening defined by the patient's nasofrontal duct to the patient's frontal sinus; and a choana.

* * * * *